US012163113B2

(12) United States Patent
Yarmush et al.

(10) Patent No.: US 12,163,113 B2
(45) Date of Patent: Dec. 10, 2024

(54) MULTILAYER STACKABLE TISSUE CULTURE PLATFORM FOR 3D CO-CULTURE

(71) Applicant: Rutgers, The State University of New Jersey, New Brunswick, NJ (US)

(72) Inventors: Martin L. Yarmush, Piscataway, NJ (US); Anil Shrirao, Piscataway, NJ (US); Rene S. Schloss, Piscataway, NJ (US); Ileana Marrero-Berrios, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 496 days.

(21) Appl. No.: 17/091,919

(22) Filed: Nov. 6, 2020

(65) Prior Publication Data
US 2021/0139833 A1    May 13, 2021

Related U.S. Application Data

(60) Provisional application No. 62/932,355, filed on Nov. 7, 2019.

(51) Int. Cl.
| | | |
|---|---|---|
| *C12M 3/00* | (2006.01) | |
| *C12M 1/00* | (2006.01) | |
| *C12M 1/12* | (2006.01) | |
| *C12M 1/32* | (2006.01) | |
| *G01N 33/50* | (2006.01) | |

(52) U.S. Cl.
CPC ............ *C12M 25/06* (2013.01); *C12M 23/12* (2013.01); *C12M 23/50* (2013.01); *C12M 25/04* (2013.01); *G01N 33/5041* (2013.01)

(58) Field of Classification Search
CPC .. C12M 25/0604; C12M 23/12; C12M 23/50; G01N 33/5041
USPC ........................................... 435/283.1
See application file for complete search history.

(56) References Cited

U.S. PATENT DOCUMENTS

| | | | | |
|---|---|---|---|---|
| 3,965,012 A | * | 6/1976 | Eguchi | B01D 63/14 |
| | | | | 210/493.1 |
| 5,536,662 A | * | 7/1996 | Humphries | C12M 25/04 |
| | | | | 435/287.4 |
| 5,962,250 A | * | 10/1999 | Gavin | B01L 3/5025 |
| | | | | 435/395 |
| 7,128,877 B2 | * | 10/2006 | Quay | G01N 33/57415 |
| | | | | 604/74 |
| 8,058,060 B2 | * | 11/2011 | Esser | C12M 23/12 |
| | | | | 435/297.5 |
| 9,829,488 B2 | | 11/2017 | Derda et al. | |

(Continued)

FOREIGN PATENT DOCUMENTS

CN         102952751 A      3/2013

OTHER PUBLICATIONS

Micro-Chem Nano SU-8 2000: Negative Tone Photoresist Formulations 2002-2025 PDF (designated as "2002-2025") (Year: 2015).*

(Continued)

*Primary Examiner* — Nathan A Bowers
(74) *Attorney, Agent, or Firm* — Michael Best & Friedrich LLP

(57) ABSTRACT

Described herein is a cell culture device and methods of use in three-dimensional cell co-cultures and for use in studying paracrine signaling in vitro.

38 Claims, 33 Drawing Sheets

(56) References Cited

U.S. PATENT DOCUMENTS

| | | |
|---|---|---|
| 2011/0105360 A1 | 5/2011 | Derda et al. |
| 2021/0087515 A1* | 3/2021 | Allbritton .............. C12M 25/02 |

OTHER PUBLICATIONS

Micro-Chem Nano SU-8 2000: Negative Tone Photoresist Formulations 2002-2025 (Web Accessed Date) (Year: 2015).*

Arango Duque et al., "Macrophage Cytokines: Involvement in Immunity and Infectious Diseases", Frontiers in Immunology, vol. 5, 2014, pp. 491-491.

Barminko et al., "Encapsulated Mesenchymal Stromal Cells for in Vivo Transplantation", Biotechnology and Bioengineering, vol. 108, No. 11, 2011, pp. 2747-2758.

Baxter et al., "Tumor Necrosis Factor-A Mediates Both Apoptotic Cell Death and Cell Proliferation in a Human Hematopoietic Cell Line Dependent on Mitotic Activity and Receptor Subtype Expression", Journal of Biological Chemistry, vol. 274, No. 14, 1999, pp. 9539-9547.

Berenbaum, "Osteoarthritis as an Inflammatory Disease (Osteoarthritis Is Not Osteoarthrosis!)", Osteoarthritis and Cartilage, vol. 21, No. 1, 2013, pp. 16-21.

Bickel, "The Role of Interleukin-8 in Inflammation and Mechanisms of Regulation", J Periodontol, vol. 64, No. 5 (Suppl), 1993, pp. 456-460.

Casillo et al., "Membrane Pore Spacing Can Modulate Endothelial Cell-Substrate and Cell-Cell Interactions", ACS Biomaterials Science & Engineering, vol. 3, No. 3, 2017, pp. 243-248.

Chen et al., "Cell Attachment and Biocompatibility of Polytetrafluoroethylene (Ptfe) Treated with Glow-Discharge Plasma of Mixed Ammonia and Oxygen", J Biomater Sci Polym Ed, vol. 14, No. 9, 2003, pp. 917-935.

Corning Inc., "Corning Cell Culture Product Selection Guide", 2015; Available from: www.corning.com/lifesciences.

Curtis et al. "Adhesion of Cells to Polystyrene Surfaces", The Journal of Cell Biology, vol. 97, No. 5, 1983, pp. 1500-1506.

Dasari et al., "A Proximal Culture Method to Study Paracrine Signaling between Cells", J Vis Exp, vol. 28, No. 138, 2018, p. 58144.

Domenech et al. "Cellular Observations Enabled by Microculture: Paracrine Signaling and Population Demographics", Integrative Biology, vol. 1, No. 3, 2009, pp. 267-274.

Fuster et al., "The Good, the Bad, and the Ugly of Interleukin-6 Signaling", The EMBO Journal, vol. 33, No. 13, 2014, pp. 1425-1427.

Goers et al., "Co-Culture Systems and Technologies: Taking Synthetic Biology to the Next Level", Journal of the Royal Society, Interface, vol. 11, No. 96, 2014, p. 20140065.

Goldring, "Culture of Immortalized Chondrocytes and Their Use as Models of Chondrocyte Function", Methods Mol Med, vol. 100, 2004, pp. 37-52.

Gray et al., "Identification of Il-1β and Lps as Optimal Activators of Monolayer and Alginate-Encapsulated Mesenchymal Stromal Cell Immunomodulation Using Design of Experiments and Statistical Methods", Biotechnology progress, vol. 31, No. 4, 2015, pp. 1058-1070.

Hedbom et al., "Molecular Aspects of Pathogenesis in Osteoarthritis: The Role of Inflammation", Cell Mol Life Sci, vol. 59, No. 1, 2002, pp. 45-53.

Huh et al., "Crosstalk between FLS and chondrocytes is regulated by HIF-2α-mediated cytokines in arthritis", Experimental & Molecular Medicine, vol. 47, No. 12, 2015, p. e197.

Itoh et al., "Il-8 Promotes Cell Proliferation and Migration through Metalloproteinase-Cleavage Prohb-Egf in Human Colon Carcinoma Cells", Cytokine, vol. 29, No. 6, 2005, pp. 275-282.

Jiao et al., "Surface Modification of Polyester Biomaterials for Tissue Engineering", Biomed Mater, vol. 2, No. 4, 2007, pp. 1748-6041.

Johnson et al., "In vitro models for the study of osteoarthritis", Vet J, vol. 209, 2016, pp. 40-49.

Juvonen et al., "Biocompatibility of Printed Paper-Based Arrays for 2-D Cell Cultures", Acta Biomaterialia, vol. 9, No. 5, 2013, pp. 6704-6710.

Kim et al., "Effect of Initial Cell Seeding Density on Early Osteogenic Signal Expression of Rat Bone Marrow Stromal Cells Cultured on Cross-Linked Poly(Propylene Fumarate) Disks", Biomacromolecules, vol. 10, No. 7, 2009, pp. 1810-1817.

Kim et al., "Fabrication of Functional 3d Hepatic Tissues with Polarized Hepatocytes by Stacking Endothelial Cell Sheets in Vitro", J Tissue Eng Regen Med, vol. 11, No. 7, 2017, pp. 2071-2080.

Klinder et al., "Comparison of Different Cell Culture Plates for the Enrichment of Non-Adherent Human Mononuclear Cells", Experimental and Therapeutic Medicine, vol. 17, No. 3, 2019, pp. 2004-2012.

Lerman et al., "The Evolution of Polystyrene as a Cell Culture Material", Tissue Eng Part B Rev, vol. 24, No. 5, 2018, pp. 359-372.

Leuning et al., "The Cytokine Secretion Profile of Mesenchymal Stromal Cells Is Determined by Surface Structure of the Microenvironment", Scientific Reports, vol. 8, No. 1, 2018, pp. 7716.

Liston et al., "Plasma Surface Modification of Polymers for Improved Adhesion: A Critical Review", Journal of Adhesion Science and Technology, vol. 7, No. 10, 1993, pp. 1091-1127.

Lotz et al., "Cartilage and Joint Inflammation. Regulation of Il-8 Expression by Human Articular Chondrocytes", The Journal of Immunology, vol. 148, No. 2, 1992, pp. 466-473.

Mathiessen et al., "Synovitis in Osteoarthritis: Current Understanding with Therapeutic Implications", Arthritis Research & Therapy, vol. 19, No. 1, 2017, pp. 18-18.

Park et al., "Paper-Based Bioactive Scaffolds for Stem Cell-Mediated Bone Tissue Engineering", Biomaterials, vol. 35, No. 37, 2014, pp. 9811-9823.

Poncin-Epaillard et al., "Surface Engineering of Biomaterials with Plasma Techniques", Journal of Biomaterials Science, Polymer Edition, vol. 14, No. 10, 2003, pp. 1005-1028.

Pu et al., "Effects of Plasma Treated Pet and Ptfe on Expression of Adhesion Molecules by Human Endothelial Cells in Vitro", Biomaterials, vol. 23, No. 11, 2002, pp. 2411-2428.

Renaud et al., "Development of an Insert Co-culture System of Two Cellular Types in the Absence of Cell-Cell Contact", J Vis Exp, vol. 17, No. 113, 2016, pp. 54356.

Rostam et al., "The Impact of Surface Chemistry Modification on Macrophage Polarisation", Immunobiology, vol. 221, No. 11, 2016, pp. 1237-1246.

Samavedi et al., "A Three-Dimensional Chondrocyte-Macrophage Coculture System to Probe Inflammation in Experimental Osteoarthritis", Tissue Engineering. Part A, vol. 23, No. 3-4, 2017, pp. 101-114.

Sapp et al., "Multilayer Three-Dimensional Filter Paper Constructs for the Culture and Analysis of Aortic Valvular Interstitial Cells"< Acta Biomaterialia, vol. 13, 2015, pp. 199-206.

Sasagawa, et al., "Design of Prevascularized Three-Dimensional Cell-Dense Tissues Using a Cell Sheet Stacking Manipulation Technology", Biomaterials, vol. 31, No. 7, 2010, pp. 1646-1654.

Simon et al., "Polymer-Based Mesh as Supports for Multi-Layered 3d Cell Culture and Assays", Biomaterials, vol. 35, No. 1, 2014, pp. 259-268.

Sitterley, "Poly-L-Lysine Cell Attachment", Protocol. BioFiles, vol. 3, No. 8, 2008, p. 12.

Slepicka, "Surface Characterization of Plasma Treated Polymers for Applications as Biocompatible Carriers", Express Polymer Letters, vol. 7, 2013 pp. 535-545.

Steele et al., "Polystyrene Chemistry Affects Vitronectin Activity: An Explanation for Cell Attachment to Tissue Culture Polystyrene but Not to Unmodified Polystyrene", J Biomed Mater Res, vol. 27, No. 7, 1993, pp. 927-940.

Tamm et al., "Cell-Adhesion-Disrupting Action of Interleukin 6 in Human Ductal Breast Carcinoma Cells", PNAS, vol. 91, No. 8, 1994, pp. 3329-3333.

(56) References Cited

OTHER PUBLICATIONS

Thomsen et al., "A Triple Culture Model of the Blood-Brain Barrier Using Porcine Brain Endothelial Cells, Astrocytes and Pericytes", PLoS One, vol. 10, No. 8, 2015, p. e0134765.
Thysen et al., "Targets, models and challenges in osteoarthritis research", Disease models & mechanisms, vol. 8, No. 1, 2015, pp. 17-30.
Tompkins et al., "Etching and Post-Treatment Surface Stability of Track-Etched Polycarbonate Membranes by Plasma Processing Using Various Related Oxidizing Plasma Systems", Plasma Processes and Polymers, vol. 11, No. 9, 2014, pp. 850-863.
Van Der Bruggen et al., "Lipopolysaccharide-Induced Tumor Necrosis Factor Alpha Production by Human Monocytes Involves the Raf-1/Mek1-Mek2/Erk1-Erk2 Pathway", Infection and Immunity, vol. 67, No. 8, 1999, pp. 3824-3829.
Walter et al., "Mesenchymal Stem Cell-Conditioned Medium Accelerates Skin Wound Healing: An in Vitro Study of Fibroblast and Keratinocyte Scratch Assays", Exp Cell Res, 2010, vol. 316, No. 7, pp. 1271-1281.
Yan et al., "Study on Microenvironment Acidification by Microfluidic Chip with Multilayer-Paper Supported Breast Cancer Tissue", Chinese Journal of Analytical Chemistry, vol. 41, No. 6, 2013, pp. 822-827.
Ng et al., "Paper based cell culture platform and its emerging biomedical applications", Materials Today, vol. 20, No. 1, 2017, pp. 32-44.
Aebersold et al., "Simple and Inexpensive Paper-Based Astrocyte Co-culture to Improve Survial of Low-Density Neuronal Networks", Frontiers in Neuroscience, vol. 12, Article 94, 2018, 14 pages.
Derda et al., "Multizone Paper Platform for 3D Cell Cultures", PLoS One, vol. 6, Issue 5, 2011, e18940.
Derda et al., "Paper-supported 3D cell culture for tissue based bioassays", PNAS, vol. 106, No. 44, 2009, pp. 18457-18462.
ThermoScientific, "Application Properties of Materials Used for Porous Membranes in Cell Culture Inserts", in Life Sciences Solutions Application Note, 2018, 4 pages.
Harada et al., "Essential involvement of interleukin-8 (IL-8) in acute inflammation", Journal of leukocyte biology, vol. 56, No. 5, 1994, pp. 559-564.
Hegemann et al., "Plasma treatment of polymers for surface and adhesion improvement", Nuclear Instruments and Methods in Physics Research Section B: Beam Interactions with Materials and Atoms, vol. 208, 2003, pp. 281-286.

\* cited by examiner

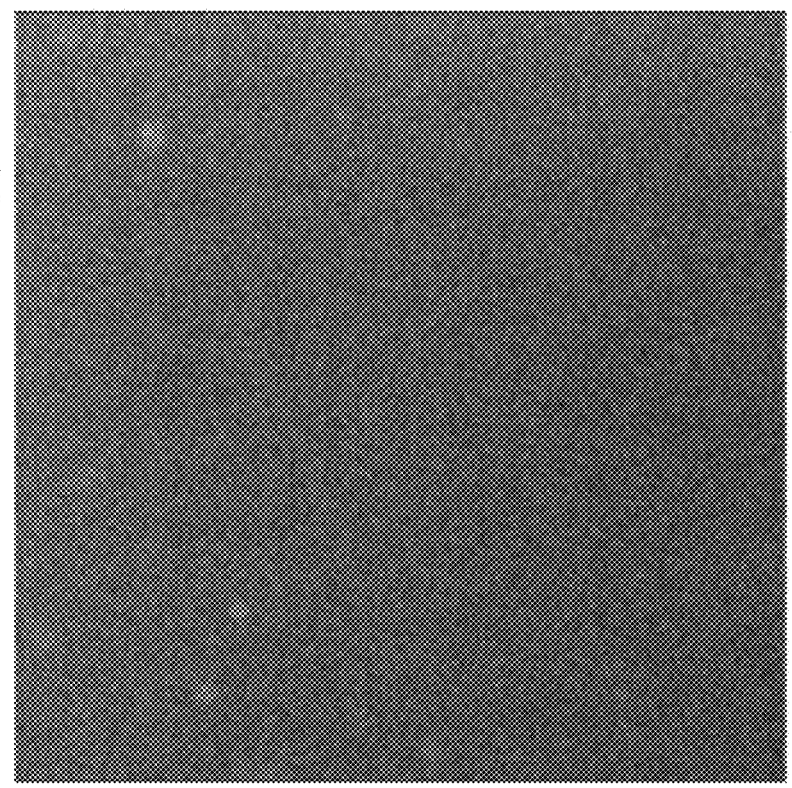
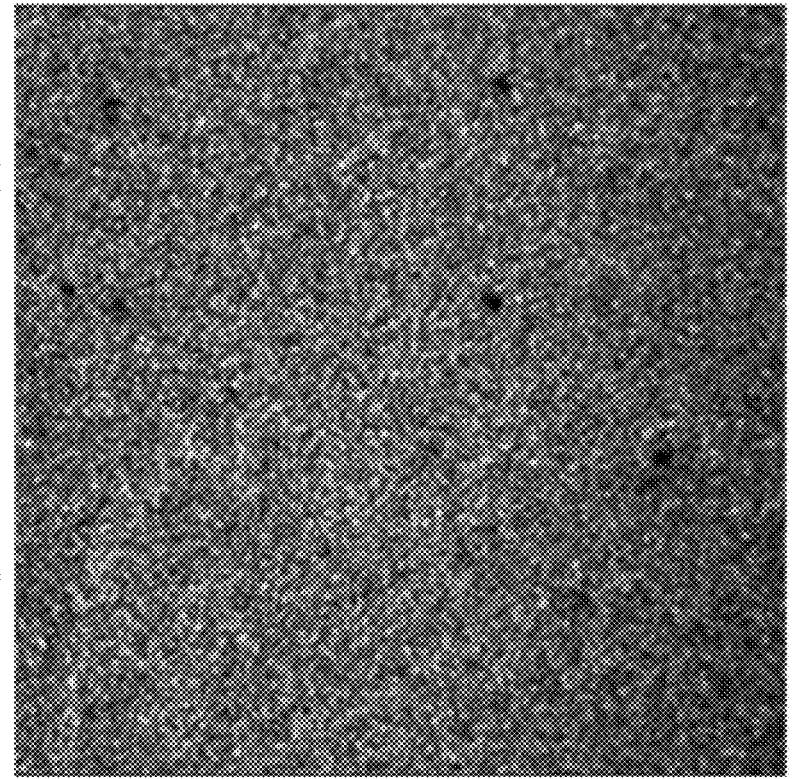
FIG. 6A

Co-culture transwell (bottom well)

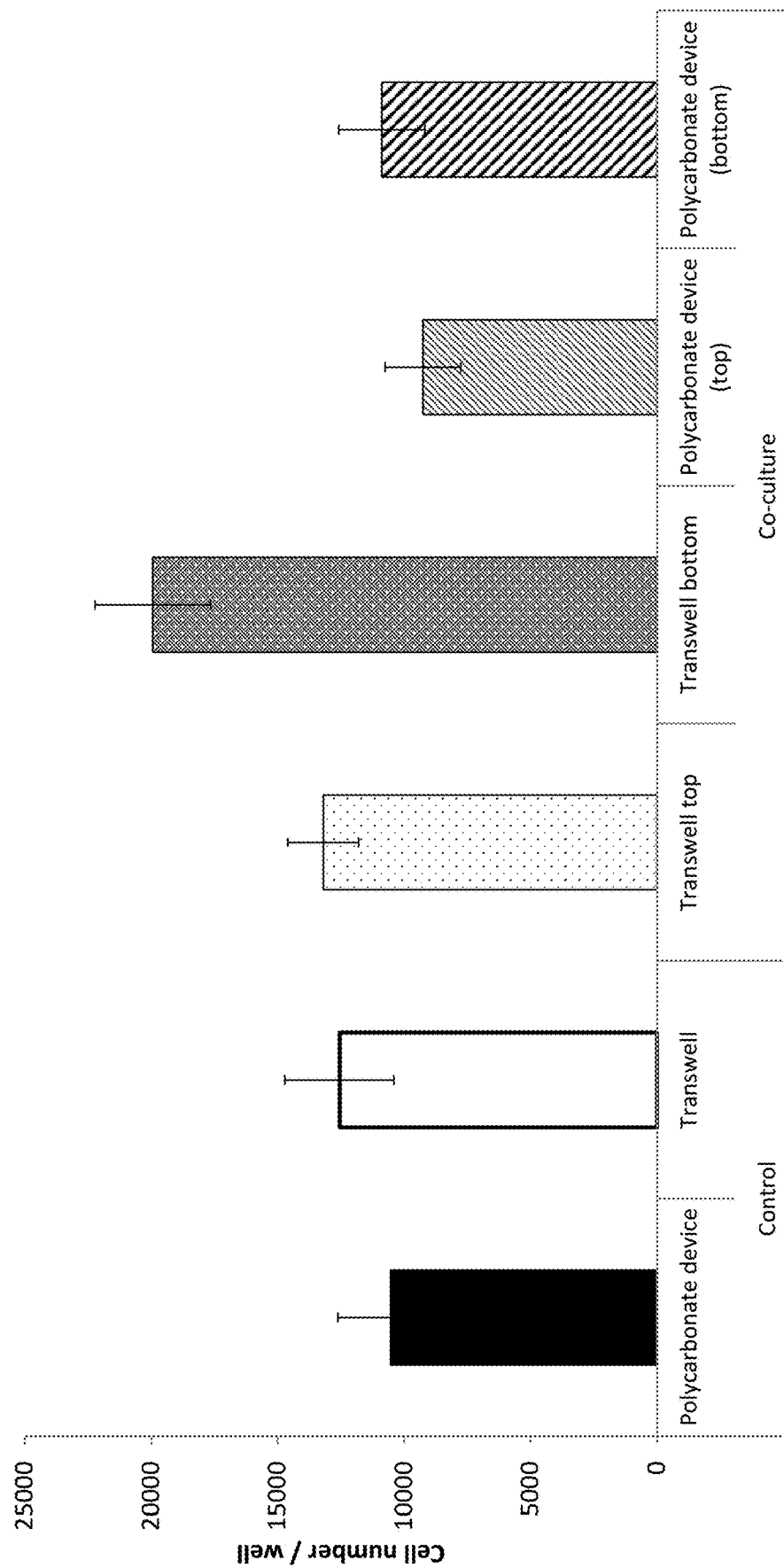
FIG. 12 MSC Cell Counts

Chondrocyte IL-8 Secretion

Macrophage IL-8 Secretion

MSC IL-8 Secretion

Chondrocyte IL-6 Secretion

MSC IL-6 Secretion

Chondrocyte Cell Number

MULTILAYER STACKABLE TISSUE CULTURE PLATFORM FOR 3D CO-CULTURE

CROSS-REFERENCE TO RELATED APPLICATIONS

This application claims priority to U.S. Provisional Patent Application No. 62/932,355, filed Nov. 7, 2019, which is incorporated herein by reference in its entirety.

FIELD

The present disclosure relates to a system that enables three-dimensional co-culture and related methods of use.

INTRODUCTION

In vitro culture and study of single cell populations helps simplify the complex relationships existing between the multiple cell types that comprise a multicellular organism. The two main advantages provided by this type of study are the reduction of confounding cellular interactions and the ability to manipulate the cellular environment to mimic in vivo-like conditions; which has allowed for the prediction of cellular behavior in vivo. However, as scientists try to simplify the cellular environment, the physiological relevance of the observed results might come into question because single cell population cultures lose the cell-cell interactions with other cell types in the vicinity, the cell-extracellular matrix interactions and 3D architecture provided by their native tissue which might be necessary for proper cell function, and the paracrine signaling between multiple cell types. To focus on questions about cell-cell and paracrine signaling interactions, scientists have relied on the use of mixed cell cultures, condition media treatments, and co-culture studies with compartmentalized cells.

Currently, the standard method to study paracrine interactions between cells in co-culture includes the use permeable retainers with microporous membranes, commonly known as transwells. These retainers were designed as hollow inserts that rest in wells from a multiwell tissue culture plate for studies of both, adherent and non-adherent cells and to study transport and other metabolic activities in vitro. For a co-culture study, one cell type is seeded in the retainer and another is seeded in the bottom well, which allows the study of paracrine signaling and the contribution of two different cell populations to the cell microenvironment. However, for more complex systems that require the study of multiple cell types that do not physically interact with one another in the native tissue, but depend on paracrine mediated signaling to retainer cell function, these permeable retainers do not suffice. For example, despite significant advances in osteoarthritis (OA) research over the past several years, a cure for OA remains elusive due, in part, to the lack of in vitro models that recapitulate the physiology and native tri-dimensional (3D) architecture of articular joint tissues. All together, these models do not consider all the components of joint tissue including: 1) all composite cell types, 2) spatial distribution of cell subsets, 3) ECM composition and its spatial distribution, and 4) mechanical properties of cartilage and bone tissue, all of which have been found to have a critical role in promoting OA inflammation. Therefore, there remains a need for an in vitro co-culture device that can accurately recreate the complex three-dimensional nature of in vivo systems.

SUMMARY

Disclosed herein is a cell culture device. The cell culture device comprises a guide collar configured to fit inside a well of a tissue culture plate, having an inner wall defining an inner space and having an axis that is parallel to the inner wall, a plurality of membrane assemblies, each comprising a planar microporous membrane on a membrane retainer, wherein each membrane retainer has a thickness between about 0.01 mm and about 1.55 mm and wherein each membrane assembly is dimensioned to fit within and translate through the inner space along the axis, and wherein the plurality of membrane assemblies includes a first membrane assembly, comprising a first planar microporous membrane and a first membrane retainer, and a second membrane assembly, comprising a second planar microporous membrane and a second membrane retainer, wherein when the first and second membrane assemblies are positioned within the inner space and the first and second planar microporous membranes are orthogonal to the axis, the first and second planar microporous membranes are parallel to one another.

Provided are methods for culturing cells. The methods comprise providing a cell culture device as disclosed herein, placing cells on each of the microporous membranes, inserting the guide collar into a well of a tissue culture plate, inserting the first membrane assembly into the guide collar whereupon the first membrane assembly translates through the guide collar until the membrane retainer engages the bottom of the tissue culture plate and the microporous membrane is orthogonal to the axis, inserting the second membrane assembly into the guide collar whereupon the second membrane assembly translates through the guide collar, the microporous membrane is orthogonal to the axis and the first and second planar microporous membranes are parallel to one another, and incubating the cells in a culture medium under conditions for growth.

Also provided are methods for studying paracrine signaling in cells. The methods comprise providing a cell culture device as disclosed herein, placing cells on each of the microporous membranes, inserting the guide collar into a well of a tissue culture plate, inserting the first membrane assembly into the guide collar whereupon the first membrane assembly translates through the guide collar until the membrane retainer engages the bottom of the tissue culture plate and the microporous membrane is orthogonal to the axis, inserting the second membrane assembly into the guide collar whereupon the second membrane assembly translates through the guide collar, the microporous membrane is orthogonal to the axis and the first and second planar microporous membranes are parallel to one another and wherein the first membrane assembly engages with the second membrane assembly and the distance between the first microporous membrane and the second microporous membrane is between about 0.01 mm and about 1.55 mm, incubating the cells in a culture medium under conditions for growth, and monitoring changes in cell behavior, cellular structures, cell morphology, cellular biomarkers or a combination thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 11 shows representative images of human chondrocytes, mesenchymal stromal cells, and macrophages after 48 hours of single culture or co-culture.

FIG. 12 is a bar graph showing mesenchymal stromal cell number per well in co-culture or single culture with chondrocytes.

FIG. 16B is graph showing the oxygen concentration along the vertical axis of the well indicated by the vertical line in FIG. 16A. Each line is representing different density of cells on each layer. The oxygen concentration for three layers with 50,000 cells per layer is at the top of the graph showing negligible effects of the multi-layer arrangement on oxygen availability.

DETAILED DESCRIPTION

Figure 1:
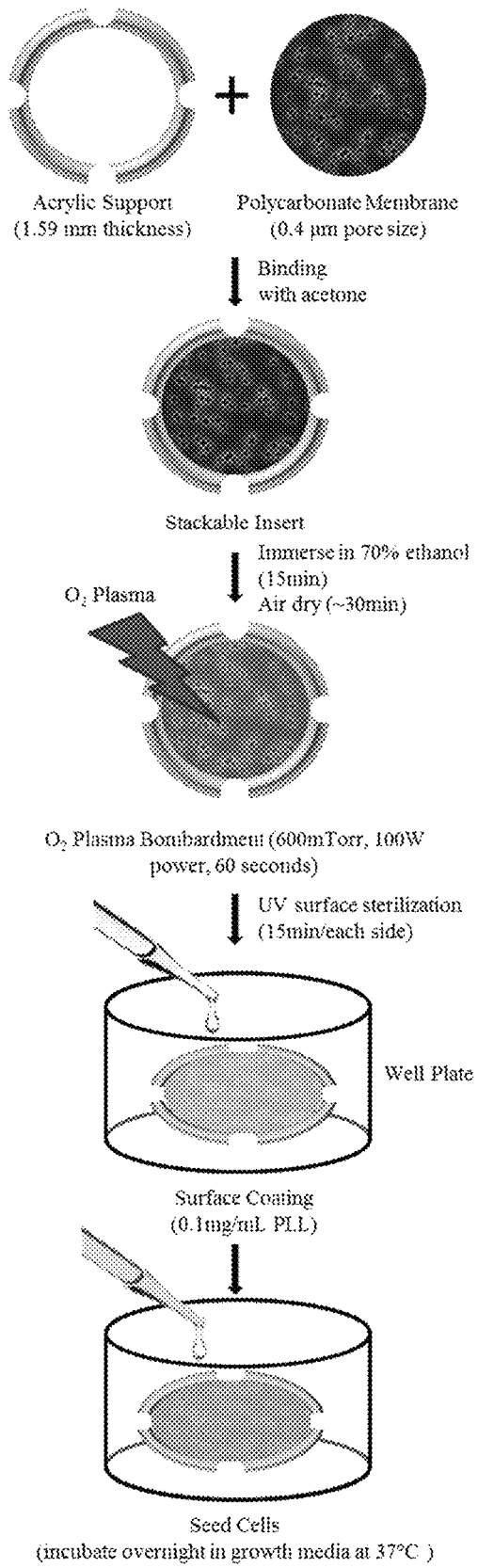
FIG. 1 is a schematic representation of the stackable insert fabrication and preparation for cell culture. A laser cut acrylic retainer was chemically bound to a polycarbonate membrane, sterilized, plasma treated, and coated with PLL to facilitate cell attachment.

The present disclosure provides methods and a device that enable three-dimensional co-culture of different types of cells. In these methods and device, membrane based assemblies are designed to culture the cells. The membrane pores are smaller than the size of the cells to stop migration while providing a scaffold for adhesion and proliferation but are large enough to allow oxygen diffusion and exchange of chemical signals between the layers above and below. The use of spacers allows the separation between two cell layers to be controlled and varied. The guide collar allows insertion and alignment of cells between layers. The device disclosed herein enables control of cell to cell and cell to microenvironment interaction such that different cell types can be seeded separately and then co-cultured together in different layers or at different times which allows for the spatialtemporal manipulation of the culture system to model the in vivo environment and mimic disease phenotypes.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, "microporous" refers to a porosity that prevents passage of eukaryotic cells but permits passage of fluids and analytes in aqueous solution. A "microporous membrane" is a membrane that prevents passage of eukaryotic cells but permits passage of analytes in aqueous solution.

2. Multilayer Tissue Culture Platform

The present disclosure provides a cell culture device comprising a guide collar configured to fit inside a well of a tissue culture plate, having an inner wall defining an inner space and having an axis that is parallel to the inner wall, a plurality of membrane assemblies, each comprising a planar microporous membrane on a membrane retainer, wherein each membrane retainer has a thickness between about 0.01 mm and about 1.55 mm and wherein each membrane assembly is dimensioned to fit within and translate through the inner space along the axis, and wherein the plurality of membrane assemblies includes a first membrane assembly, comprising a first planar microporous membrane and a first membrane retainer, and a second membrane assembly, comprising a second planar microporous membrane and a second membrane retainer, wherein when the first and second membrane assemblies are positioned within the inner space and the first and second planar microporous membranes are orthogonal to the axis, the first and second planar microporous membranes are parallel to one another. Exemplary embodiments of the cell culture device are described in detail below with respect to FIGS. 1-5.

Figure 2:
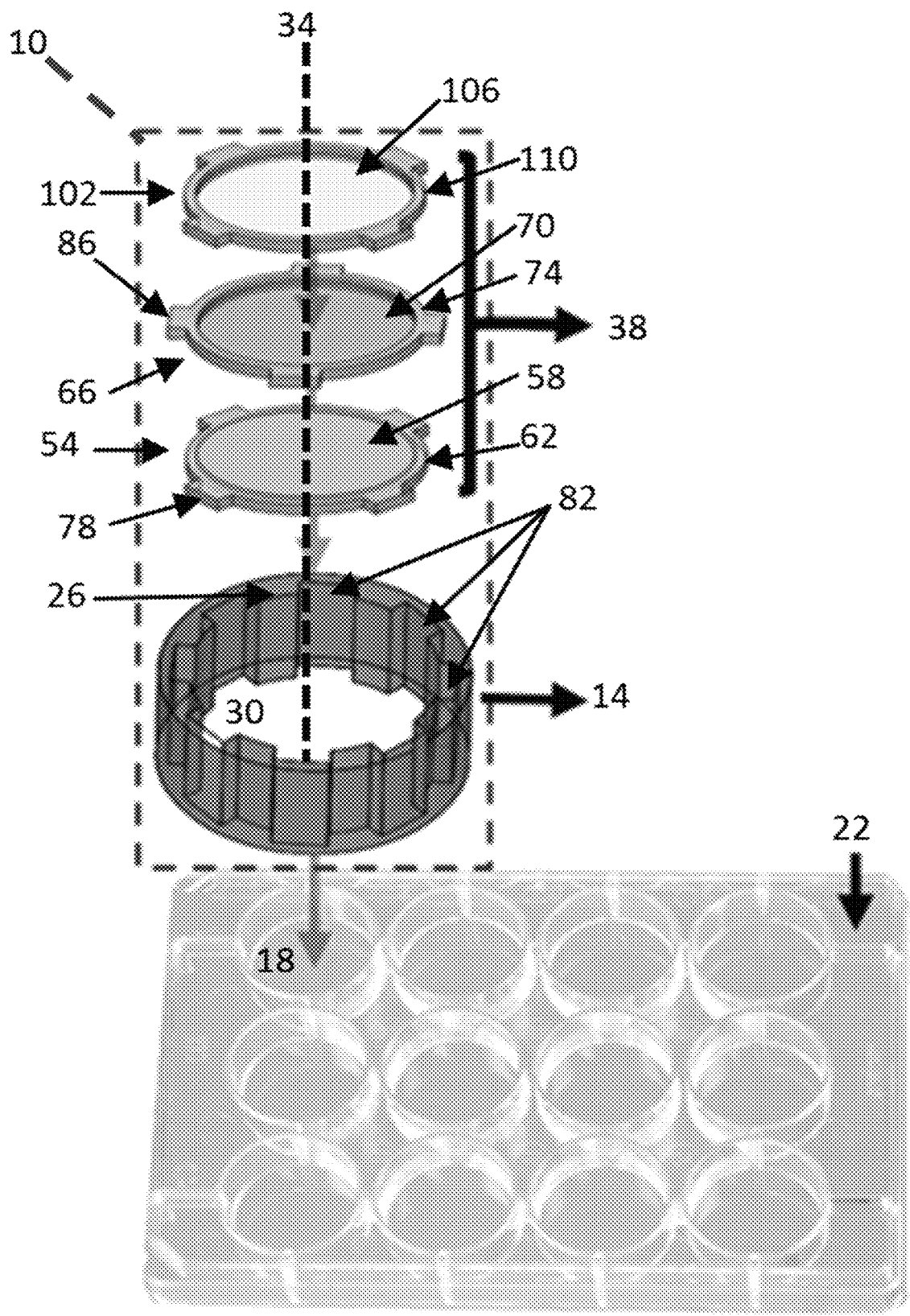
FIG. 2 is a schematic showing one embodiment of the cell culture device 10 disclosed herein.

FIG. 2 shows an exemplary cell culture device 10 in accordance with an embodiment of the present disclosure. The cell culture device 10 includes a guide collar 14 and a plurality of membrane assemblies 38.

The guide collar 14 is configured to fit inside a well 18 of a tissue culture plate 22. The guide collar 14 may be of any size or shape necessary to fit inside of the well 18 of a tissue culture plate 22. For example, the tissue culture plate 22 may include a matrix of wells 18 having dimensions of 4×6 (24 wells), 8×12 (96 wells), 16×24 (384 wells), or 32×48 (1536 wells). The guide collar 14 may be in the shape of a circle, a square or an oval. In some embodiments, the guide collar 14 is in the shape of a circle. The guide collar 14 has an inner wall 26 defining an inner space 30 and having an axis 34 that is parallel to the inner wall 26.

Figure 3:
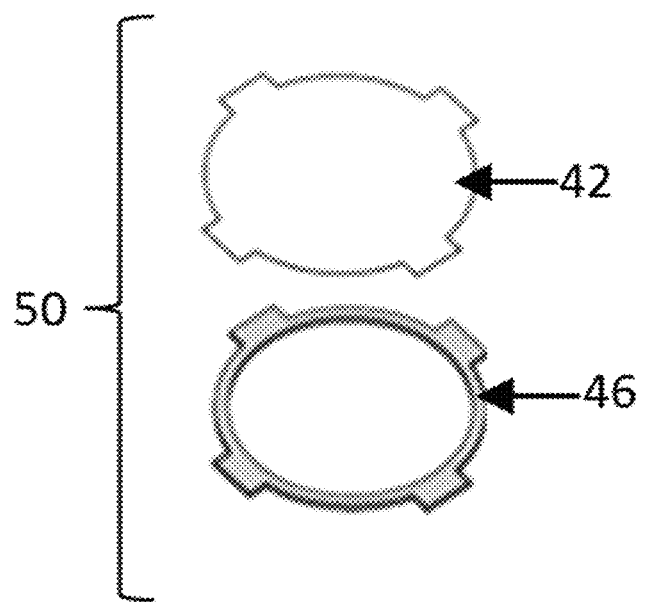
FIG. 3 is a schematic showing a membrane assembly including a microporous membrane 42 and a membrane retainer 46.

The plurality of membrane assemblies 38 each comprise a planar microporous membrane 42 on a membrane retainer 46, as shown for a single membrane assembly 50 in FIG. 3. The planar microporous membrane 42 may be attached to the membrane retainer 46 by any conventional means known in the art. For example the planar microporous membrane 42 may be attached to the membrane retainer 46 using either chemical bonding, such as acetone, or adhesive bonding, such as a biocompatible epoxy. Each membrane retainer 46 has a thickness between about 0.01 mm and about 1.55 mm. Each membrane assembly 50 is dimensioned to fit within and translate through the inner space 30 along the axis 34.

The plurality of membrane assemblies 38 includes: a first membrane assembly 54 comprising a first planar microporous membrane 58 and a first membrane retainer 62 and a second membrane assembly 66 comprising a second planar microporous membrane 70 and a second membrane retainer 74. The first and second membrane assemblies, 54 and 66, are positioned within the inner space 30 and the first and second planar microporous membranes, 58 and 70, are orthogonal to the axis 34. The first and second planar microporous membranes, 58 and 70, are also parallel to one another.

The cell culture device 10 may comprise at least three membrane assemblies. As such, the exemplary embodiment of the cell culture device 10 in FIG. 2 includes a third membrane assembly 102 comprising a third planar microporous membrane 106 and a third membrane retainer 110. Each microporous membrane 42 may comprise microporous polymeric material such as linear polycarbonates, polyesters of carbonic acid, poly(vinylchloride), polyamides, styrene-acrylic acid copolymers, polysulfones, halogenated poly (vinylidene), polychloroethers, poly(urethanes), poly(imides), glass and polyethylene terephthalate (PET or PETE). The membrane may be translucent. The membrane may be clear or transparent to allow visualization of cell by light microscopy.

Each microporous membrane 42 allows for exchange of media, nutrients and molecules. However, the pores of the microporous membrane 42 are also sized to isolate the cells on each membrane assembly 50 from those cells on the adjacent membrane assembly 50 by restricting passage of cells through the microporous membrane 42. The pore size will be dependent on cell type but will generally range from 0.2 µm to 1.0 µm. Larger pore diameters, greater than 3.0 µm, tend to allow cell passage. As such, in this device to avoid cell passage, the diameter of the pores of the microporous membrane should be less than or equal to about 3.0 µm. For example, less than or equal to 2.5 µm, less than or equal to 2.0 µm, less than or equal to 1.5 µm, less than or equal to 1.0 µm, less than or equal to 0.5 µm.

The first membrane retainer 62 may comprise a first tab 78. The inner wall 26 of the guide collar 14 may include one or more grooves 82. Each of the one or more grooves 82 is parallel to the axis 34 and is configured to receive the first tab 78 and direct the first membrane assembly 54 as it translates through the inner space 30.

When the first membrane assembly 54 is positioned within the inner space 30 and the first tab 78 is engaged with a first groove of the one or more grooves 82, the first groove and the first tab 78 inhibit rotation of the first membrane assembly 54 about the axis 34.

The second membrane retainer 74 may comprise a second tab 86. Each of the one or more grooves 82 is parallel to the axis 34 and is configured to receive the second tab 86 and direct the second membrane assembly 66 as it translates through the inner space 30.

The inner wall 26 of the guide collar 14 may include one or more grooves 82. The first membrane retainer 62, the second membrane retainer 74, or both the first membrane retainer 62 and the second membrane retainer 74 may comprise a plurality of tabs, each position to engage a different one of the plurality of grooves 82.

The membrane retainer 46 may include an aperture 86. The microporous membrane 42 extends across the aperture. The surface area of each microporous membrane 42 is substantially the same.

The microporous membrane 42 may be coated with at least one biomaterial wherein the biomaterial comprises proteins, polypeptides, amino acids, polysaccharides, monosaccharides or a combination thereof. Preferably, the biomaterial facilitates attachment of cells to the microporous membrane, for example, by ionic or covalent bonding. Examples of suitable biomaterials include extracellular matrix molecules (ECMs), such as laminins, tenascins, collagens, netrins, semaphorin, thrombospondin, fibronectin, vitronectin, proteoglycan and fragments thereof. The biomaterial may include cell-cell adhesion molecules (CAMs), such as cadherin superfamily or immunoglobulin (Ig) superfamily molecules (NCAM or fibronectins). The biomaterial may also include angiogenic factors or growth factors. The biomaterials can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals. In some embodiments, the biomaterial is poly-L-Lysine (PLL).

Figure 4:
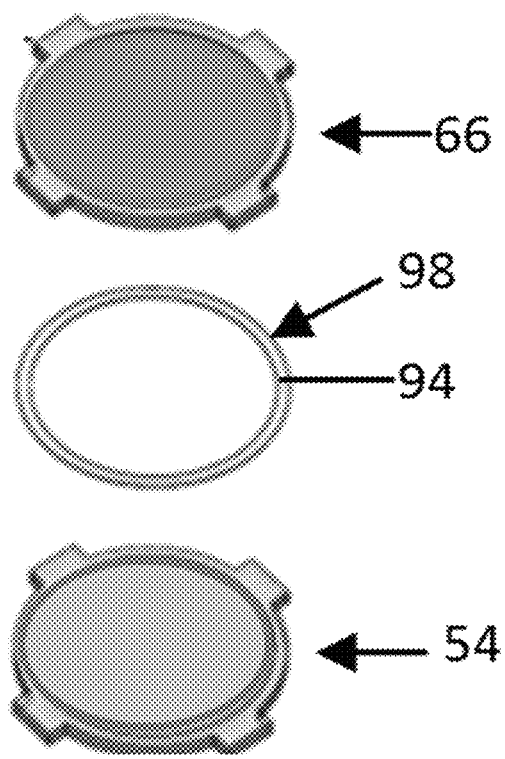
FIG. 4 is a schematic showing an alternate embodiment of the cell culture device wherein a spacer 94 is positioned between a first membrane assembly 54 and a second membrane assembly 64.

FIG. 4 shows an alternate embodiment of the cell culture device 10 wherein the device further comprises at least one spacer 90. The spacer 90 is adapted to be positioned between the first membrane assembly 54 and the second membrane assembly 66 of the cell culture device 10.

Figure 5A:
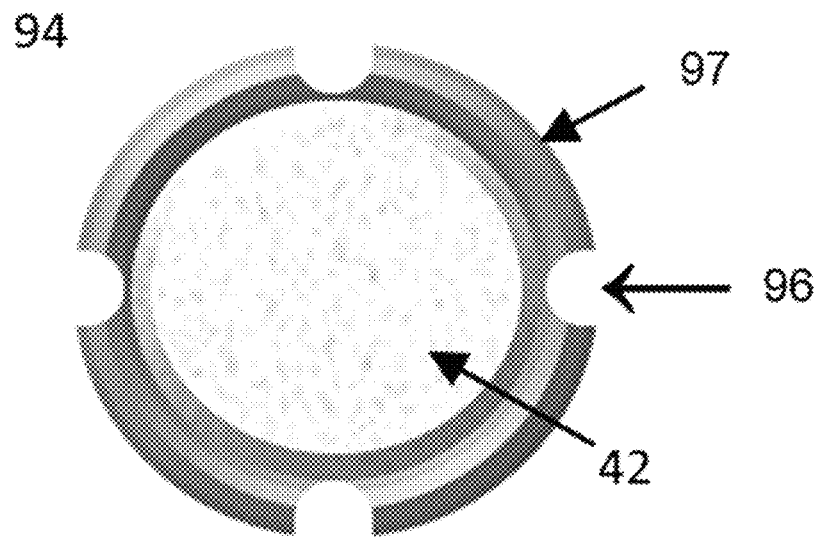
FIG. 5A and FIG. 5B are schematics showing different embodiments of membrane assembly including a microporous membrane 42 and retainer 97.
Figure 5B:
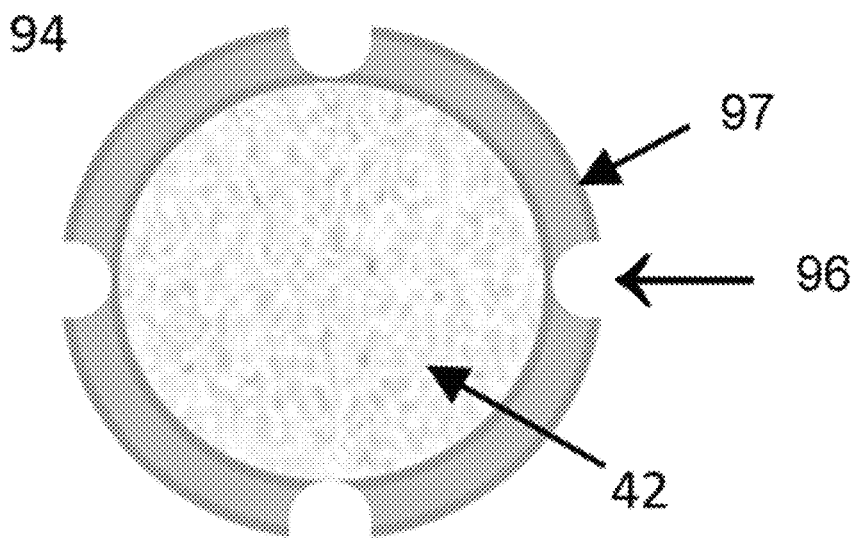

The spacer 90 has an outer wall 98 shape and dimension corresponding to the inner wall 26 of the guide collar 14 such that the spacer 90 translates through the inner space 30 along and orthogonal to the axis 34. The spacer 90 may be about 0.01 mm to about 1.55 mm thick. FIG. 5A and FIG. 5B illustrate two additional embodiments of the microporous membrane 42 and retainer 97. The notches 96 on the retainer 97 engage with tabs 26 on the guide collar 14. Tweezers may be used to place the membrane assembly 66 into the well 18 of the culture dish 22. The notches 96 in the retainer 97 allow easy removal of tweezers from the well 18 without disrupting the membrane assembly 66.

Fabrication of the Microporous Membrane Layers that Exhibit High Modulus of Elasticity to Prevent Self-Buckling.

The cell culture membrane may be fabricated using glass to overcome the self-buckling of the material. The cell culture microporous membrane is a critical component of multilayer stackable culture systems. The membrane should be made from a biocompatible material and support the growth of different types of cells. In addition, the two cell layers should be isolated to separate these layers from each other as per the need of experiments for further single layer characterization. As a result, the membrane layer, after culturing cells, should be free from self-buckling to prevent physical contact between adjacent layers. The membrane layer should also be suitable for functionalization with different cell adhesion molecules as required by different cell types. The pores in the membrane should be small enough to prevent cell migration but large enough to support the diffusion of biomolecules, either secreted by cells or present in the culture media. Lastly, the membrane material should be transparent for imaging and inexpensive for a low-cost stackable culture system.

The membrane will be fabricated using a 25 µm thin glass wafer (AF 32® eco, SCHOTT North America Inc., Elmsford, NY 10523). The thin layer of aluminum (3-5 µm) will deposited using physical vapor deposition (PVD) on the glass substrate to provide it with mechanical stability during handling and act as a mask for scaffold pattern etching. The positive photoresist (Shipley 1813, MicroChem Inc, MA) will be spin coated on the aluminum layer and UV patterned (micropores) using the scaffold photo mask. The scaffold mask will consist of micropores of diameter 1-3 µm arranged in a random order in a circular area equal to area of glass membrane. The aluminum exposed from the patterned photoresist will be etched using aluminum etchant. The photoresist will be then stripped off, exposing patterned aluminum which will act as a mask for further etching. Then, deep reactive ion etching (DRIE) will be used to etch the glass, creating through-holes in the glass, thereby making porous glass membranes. After fabrication of the membrane, we will evaluate the buckling of the porous membrane under loading and no loading conditions. The loading will be performed using physical incremental weights and then recording the buckling profile. The visual observation of buckling at the time of loading will be captured using a digital camera situated perpendicular to the membrane. We will determine the loading limits that creates insignificant bending and compare it to the loading weight when the membrane layer is confluent with cells to determine the threshold acceptable for cell loading.

Fabrication of Circular Rim to Retain the Cell Culture Membrane Layer and Facilitate Layer to Layer Assembly.

The rim will provide the structural strength for the scaffold layer as well as will define the separation between two layers. The separation between the layers may be close to 25 µm which is on the of the order of single cells. The rim will be fabricated using a biocompatible high-density polymer such as negative photoresist SU8, often used in fabrication of devices for tissue engineering. The high-density polymer will ensure that it will be submerged under culture media and not float on top. The biocompatibility of this material will ensure that the cell growth as well as function will be unaffected. The photoresist can be easily patterned using UV exposure and thus provides flexibility in design and engineering the photoresist structure. In addition, it is transparent and compatible with the microfabrication process and has previously demonstrated strong bonding with glass substrates. This will facilitate the integration of the rim and membrane using conventional microfabrication methodologies.

The rim will be fabricated by integrating it directly on the membrane layer. For this, a 25 µm layer of the negative photoresist SU8-2500 will be spin coated on the scaffold layer and soft baked on a hot plate. The circular rim will be UV patterned using rim photomask. The excess photoresist will be removed in SU8 developer after completion of post-exposure baking. The two-layer assembly is then rinsed with isopropanol and dried with nitrogen. The entire assembly is then treated inside with plasma cleaner to render the surface of the assembly hydrophilic for subsequent processing. In this way, we will microfabricate two-layer cell culture scaffold layers. The thickness of the rim will be evaluated using a profilometer and the spinning recipe will be optimized to obtain a thickness in the range of 20-30 µm to achieve variable inter-layer separation as per the requirements of the different cell types and experiments.

In addition, we will also fabricate glass rings using the process described in the previous section. This ring will serve as an additional spacer if there is a need to increase the inter-layer distance depending on the requirements of the experiment.

3. Methods of Three-Dimensional Co-Culture i. A Method for Culturing Cells In Vitro The present disclosure also provides a method of culturing cells in vitro. The method comprises providing a cell culture device as disclosed herein, placing cells on each of the microporous membranes 42, inserting the guide collar 14 into a well 18 of a tissue culture plate 22, inserting the first membrane assembly 54 into the guide collar 14 whereupon the first membrane assembly 54 translates through the guide collar 14 until the first membrane retainer 62 engages the bottom of the tissue culture plate 22 and the first microporous membrane 58 is orthogonal to the axis 34, inserting the second membrane assembly 66 into the guide collar 14 whereupon the second membrane assembly 66 translates through the guide collar 14, the second microporous membrane 70 is orthogonal to the axis 34 and the first and second planar microporous membranes 58 and 70 are parallel to one another, and incubating the cells in a culture medium under conditions for growth.

The first membrane assembly 54 engages with the second membrane assembly 66. The distance between the first microporous membrane 58 and the second microporous membrane 70 is between about 0.01 mm and about 1.55 mm.

The method may further include inserting a third membrane assembly 102 into the guide collar 14. The third membrane assembly 102 translates through the guide collar 14. The third microporous membrane 106 is orthogonal to the axis 34. The second membrane assembly 66 may engage with the third membrane assembly 102. The second and third microporous membranes 70 and 106 are parallel to one another. The distance between the second microporous membrane 70 and the third microporous membrane 106 is between about 0.01 mm and about 1.55 mm.

The method may further include selecting the plurality of spacers 94 and positioning the plurality of spacers 94 between the first membrane assembly 54 and the second membrane assembly 66, the second membrane assembly 66 and the third membrane assembly 102, or a combination thereof.

The method may further include coating the microporous membrane 42 with at least one biomaterial wherein the biomaterial comprises proteins, polypeptides, amino acids, polysaccharides, monosaccharides or a combination thereof.

The method may further include comprising incubating the membrane assemblies 50 in a culture medium under conditions for cell growth separately prior to loading into the guide collar 14.

Each of the microporous membranes 42 may include multiple types of cells or a single cell type. The cells on each of the microporous membranes 42 of the membrane assemblies 50 may be the same or different types of cells. In some embodiments, the cells on at least one of the microporous membranes of the membrane assemblies are different types of cells. In some embodiments, the cells on each of the microporous membranes of the membrane assemblies are different types of cells.

Each of the membrane assemblies 50 may be loaded into the guide collar 14 at the same time. In some embodiments, at least one of the membrane assemblies is loaded into the guide collar 14 at a different time. In some embodiments, each of the membrane assemblies is loaded into the guide collar 14 at a different time. For instance, a researcher can place a media in the tissue culture well 18 configured with the guide collar 14 and then place the first membrane assembly 62 in the guide collar 14 then the second membrane assembly 66 may be placed in the guide collar 14 immediately following or a given length of time later.

By selecting which of the tabs on each of the membrane retainers 46 of membrane assemblies 50 engage with which of the one or more grooves 82, the alignment of cells can be controlled. In some embodiments, the first tab 78 of the first membrane retainer 62 may engage with the same groove as the second tab 86 of the second membrane retainer 74 thereby aligning the cells on the first microporous membrane 58 and the second microporous membrane 70. In some embodiments, the first tab 78 of the first membrane retainer 62 may engage with a different groove from that of the second tab 86 of the second membrane retainer 74, thereby not aligning the cells on the first microporous membrane 58 with those on the second microporous membrane 70.

ii. A Method for Studying Paracrine Signaling in Cells

The present disclosure also provides a method for studying paracrine signaling in cells in vitro. The method comprises providing a cell culture device as disclosed herein, placing cells on each of the microporous membranes 42, inserting the guide collar 14 into a well 18 of a tissue culture plate 22, inserting the first membrane assembly 54 into the guide collar 14 whereupon the first membrane assembly 54 translates through the guide collar 14 until the first membrane retainer 62 engages the bottom of the tissue culture plate 22 and the first microporous membrane 58 is orthogonal to the axis 34, inserting the second membrane assembly 66 into the guide collar 14 whereupon the second membrane assembly 66 translates through the guide collar 14, the second microporous membrane 70 is orthogonal to the axis 34 and the first and second planar microporous membranes 58 and 70 are parallel to one another, incubating the cells in a culture medium under conditions for growth and monitoring changes in cell behavior, cellular structures, cell morphology, cellular biomarkers or a combination thereof.

The first membrane assembly 54 engages with the second membrane assembly 66. The distance between the first microporous membrane 58 and the second microporous membrane 70 is between about 0.01 mm and about 1.55 mm.

The method may further include inserting a third membrane assembly 102 into the guide collar 14. The third membrane assembly 102 translates through the guide collar 14. The third microporous membrane 106 is orthogonal to the axis 34. The second membrane assembly 66 may engage with the third membrane assembly 102. The second and third microporous membranes 70 and 106 are parallel to one another. The distance between the second microporous membrane 70 and the third microporous membrane 106 is between about 0.01 mm and about 1.55 mm.

The method may further include selecting the plurality of spacers 94 and positioning the plurality of spacers 94 between the first membrane assembly 54 and the second membrane assembly 66, the second membrane assembly 66 and the third membrane assembly 102, or a combination thereof.

The method may further include coating the microporous membrane 42 with at least one biomaterial wherein the biomaterial comprises proteins, polypeptides, amino acids, polysaccharides, monosaccharides or a combination thereof.

The method may further include comprising incubating the membrane assemblies 50 in a culture medium under conditions for cell growth separately prior to loading into the guide collar 14.

The cells on each of the microporous membranes 42 of the membrane assemblies 50 may be the same or different types of cells. In some embodiments, the cells on at least one of the microporous membranes of the membrane assemblies are different types of cells. In some embodiments, the cells on each of the microporous membranes of the membrane assemblies are different types of cells.

Each of the membrane assemblies 50 may be loaded into the guide collar 14 at the same time. In some embodiments, at least one of the membrane assemblies is loaded into the guide collar 14 at a different time. In some embodiments, each of the membrane assemblies is loaded into the guide collar 14 at a different time.

Monitoring changes in cell behavior, cellular structures, cell morphology and cellular biomarkers may be done by any method known to one of skill in the art including, but not limited to, microscopy, immunohistochemistry, microarray analysis, chromatography, mass spectrometry, flow cytometry, electrophoresis, or affinity assays.

4. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

Example 1

Materials, chemicals and reagents: High glucose Dulbecco's Modified Eagle Medium (hgDMEM), Minimum Essential Medium-alpha (MEM-α), Advanced RPMI 1640 Medium, fetal bovine serum (FBS) (Gibco), L-glutamine (Gibco), penicillin/streptomycin (Gibco), basic fibroblast growth factor (bFGF) (Gibco), calcein AM (Molecular Probes), ethidium homodimer (Molecular Probes) and Hoechst 33342 (Invitrogen) were purchased from Thermo Fisher Scientific (Waltham, MA). Poly-L-Lysine (PLL) and FITC-labeled PLL were purchased from Millipore Sigma (Burlington, MA). Polymeric microporous membranes were purchased from Sterlitech Corporation (Kent, WA). Membrane retainer materials were purchased from McMaster-Carr (Elmhurst, IL).

Cell culture: All cells were maintained in a humidified 37° C. incubator with 5% $CO_2$ and cultured in their respective medias until used for experiments. The C28/I2 human chondrocyte cell line was obtained from Mary Goldring's Laboratory at the Hospital for Special Surgery Research Institute (New York, NY) and was cultured using hgDMEM supplemented with 10% FBS, 1% penicillin/streptomycin, and 2 mM L-glutamine. Human bone morrow-derived mesenchymal stromal cells (MSCs) were purchased from the Institute for Regenerative Medicine (Texas A&M College of Medicine, Temple, TX) and grown on MEM-α containing 10% FBS, 2 mM L-glutamine, 1% penicillin streptomycin and 1 ng/mL bFGF. Macrophages were obtained from peripheral blood mononuclear cells collected from blood of healthy human donors (New York Blood Center) by enriching the $CD14^+$ cell population, using magnetic cell sorting (Miltenyi Biotech, Auburn, CA) and cultured in Advanced RPMI (Gibco). Advanced RPMI was supplemented with 10% FBS, 1% penicillin streptomycin, and 4 mM L-glutamine.

Example 2

Figure 16A:
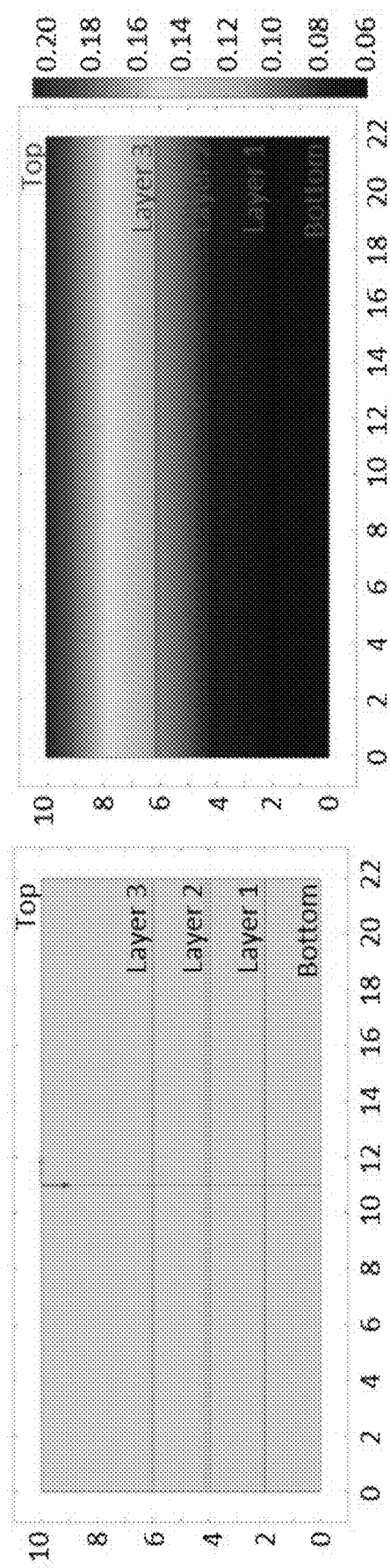
FIG. 16A and FIG. 16B show the effect of the multi-layer arrangement on oxygen distribution. A cross section of a well filled with media up to 10 mm and consisting three cell layers is shown in the left panel of FIG. 16A. The distribution of concentration of oxygen in the well with 400,000 cells per layer is shown in the right panel of FIG. 16A.
Figure 16B:
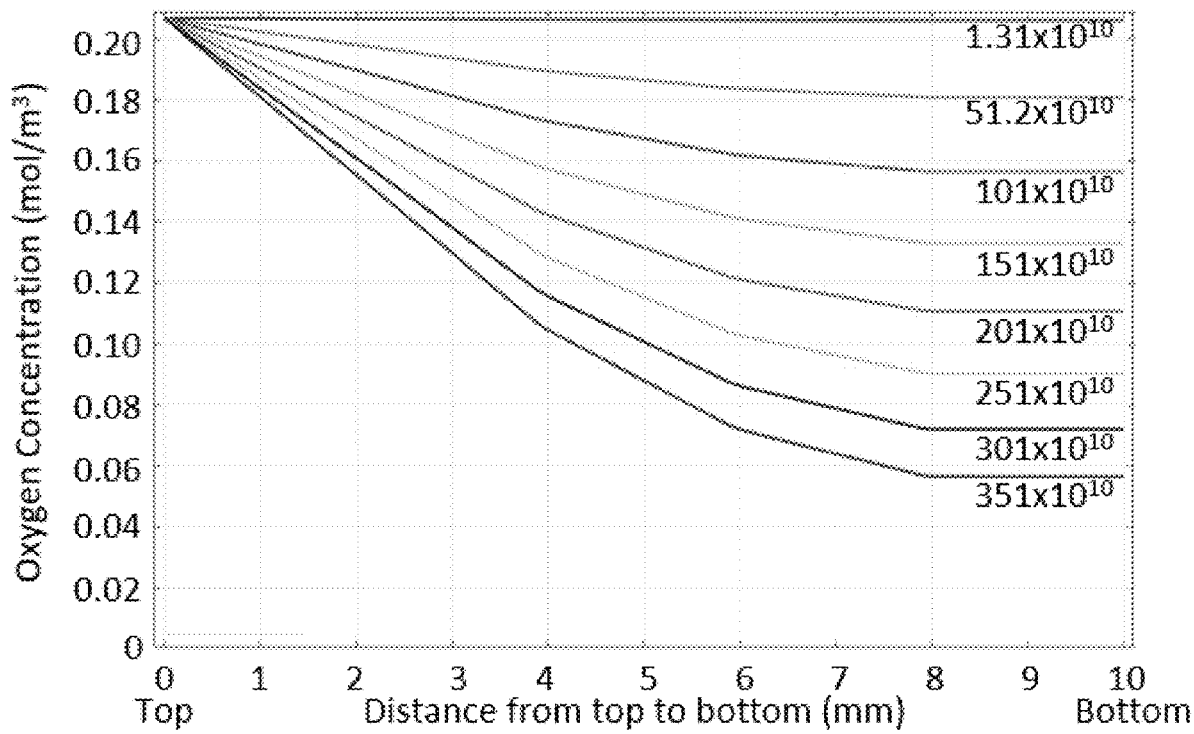
Figure 17A:
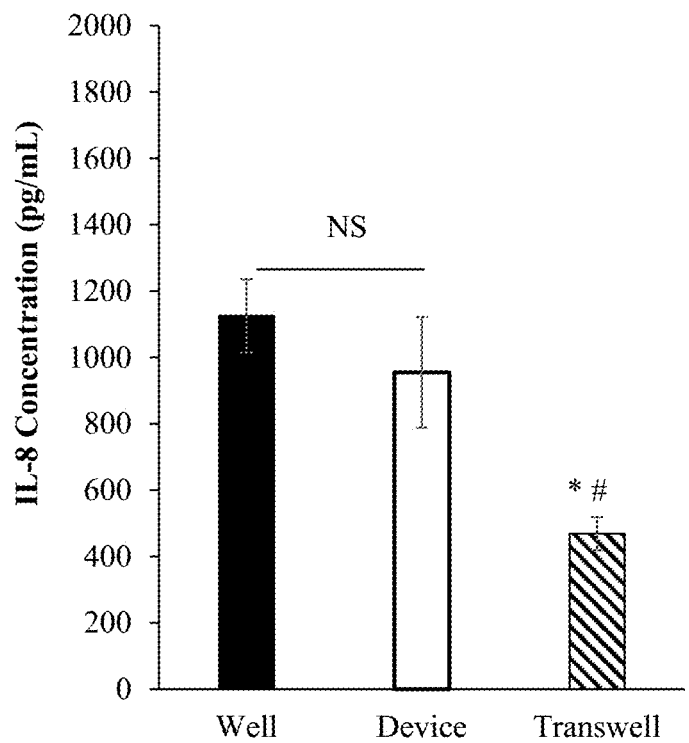
FIG. 17 shows cell cytokine secretion in different growth surfaces. IL-8 and IL-6 levels for FIG. 17A/FIG. 17D) chondrocytes, FIG. 17B) macrophages, and FIG. 17C/FIG. 17E) MSCs were measured from the cell culture supernatants after 48 hours of culture. TNF-α was not detected in any of the cell types and IL-6 was not detected in the macrophage cultures. Bar graphs represent the average cell secretion±SEM (pg/mL) of 3 independent experiments (P<0.05 as compared to Well (*), Device (#), or Transwell (+) by ANOVA with Fisher's LSD post hoc test). NS=not significant.
Figure 17B:
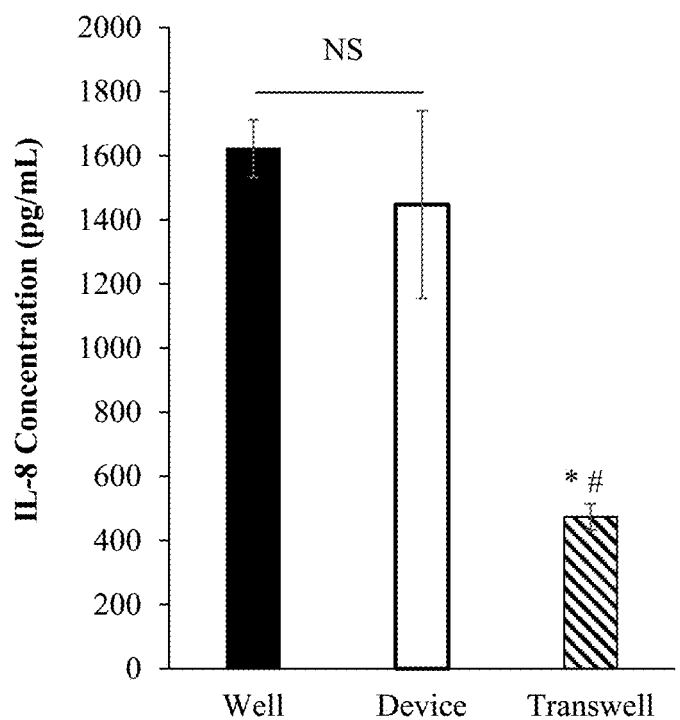
Figure 17C:
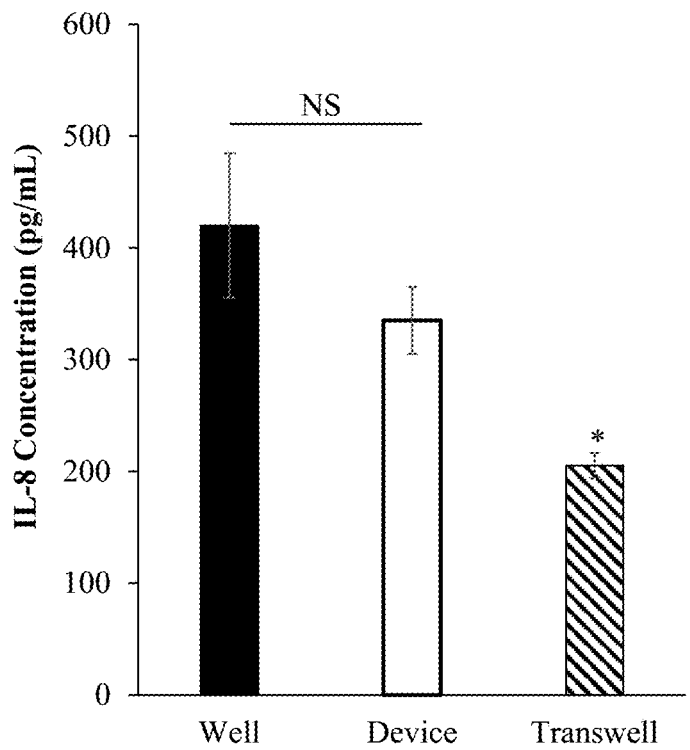
Figure 17D:
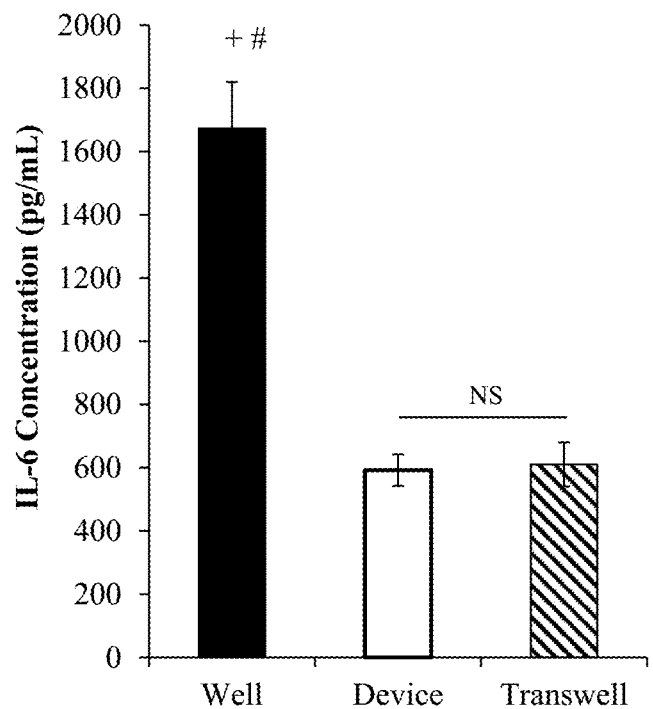
Figure 17E:
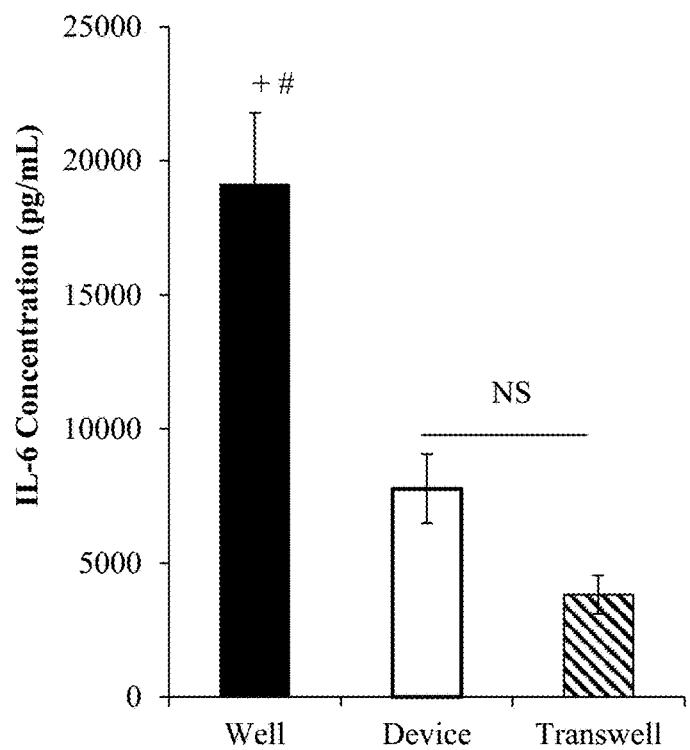
Figure 18A:
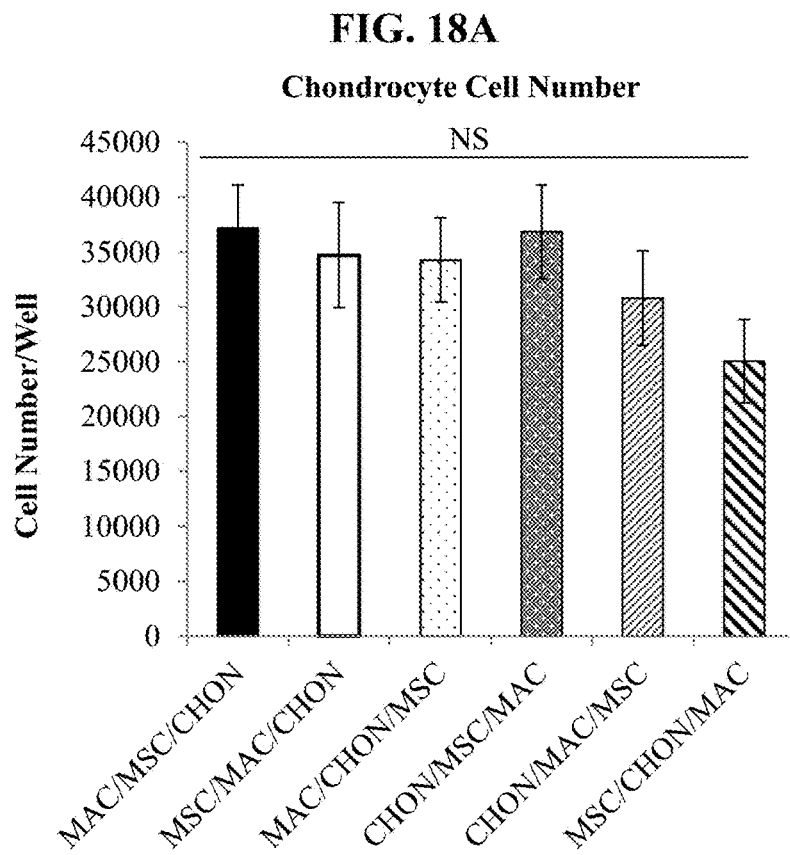
FIG. 18A) chondrocyte cell counts, FIG. 18B) macrophage cell counts, FIG. 18C) MSC cell counts, and FIG. 18D) total cell counts of different culture configurations. CHON=chondrocytes, MAC=macrophages and MSC=mesenchymal stromal cells. Bar graphs represent the average cell counts per well±SEM of n=6-12 samples from at least 3 independent experiments (P<0.05 as compared to configuration #3 (*) or configuration #4 (#) by ANOVA with Fisher's LSD post hoc test). NS=not significant.
Figure 18B:
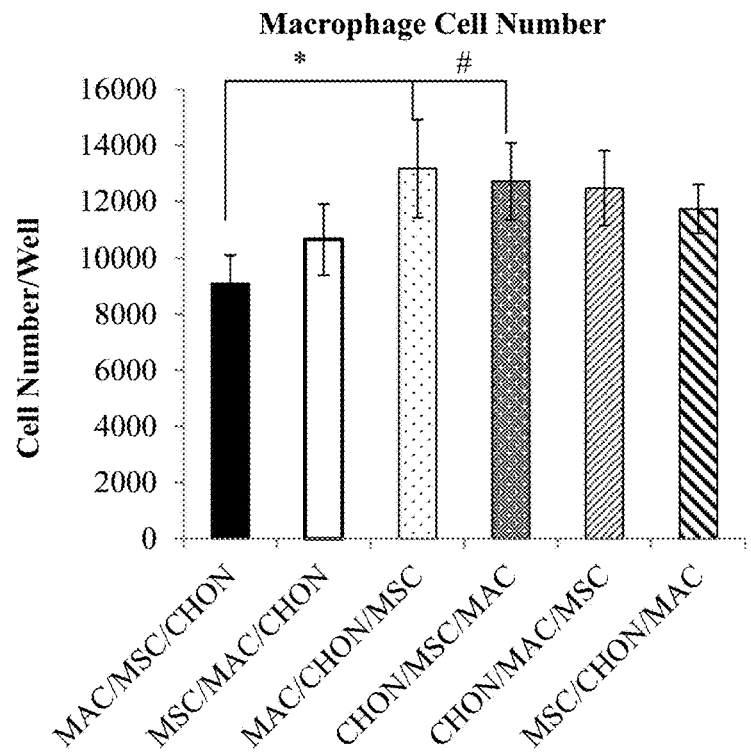
FIG. 18 shows different cell types cultured for 48 hours in multiple stack configurations. X-axis indicates the configuration type and the location of the cells (Top/Middle/Bottom).
Figure 18C:
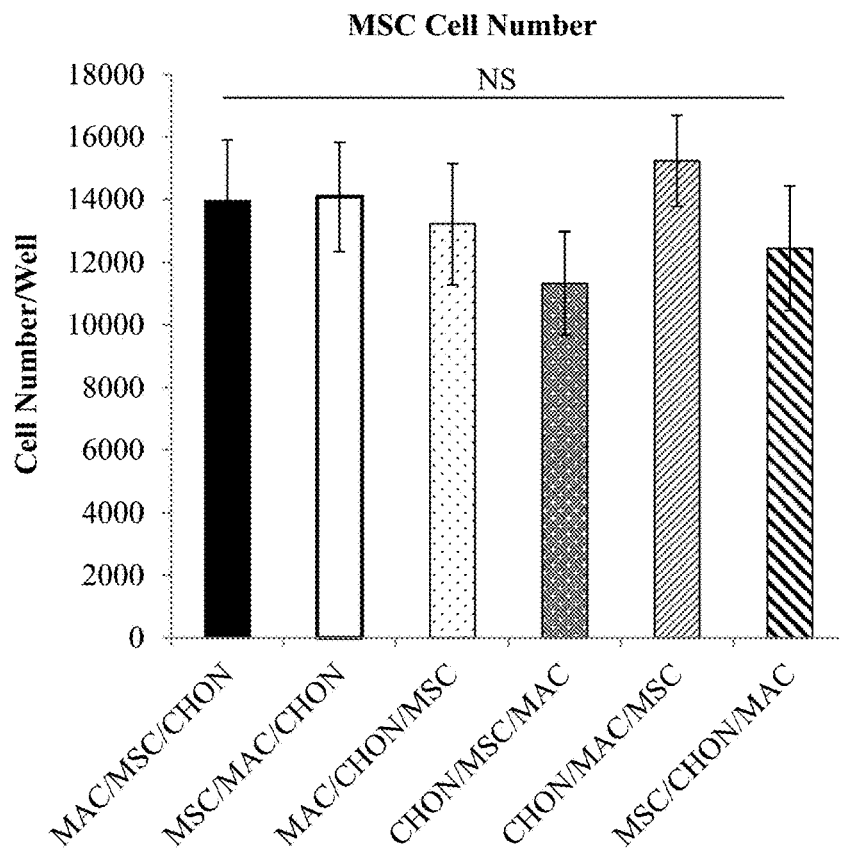
Figure 18D:
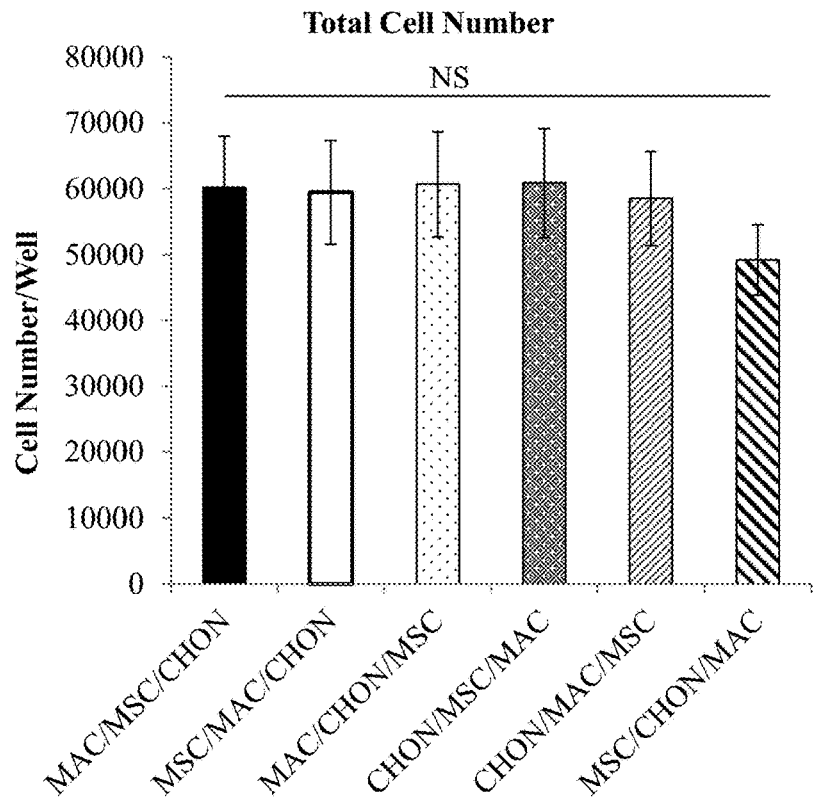

$O_2$ Diffusion Modeling. Oxygen transport could be a limiting factor for tissue culture if not enough oxygen reaches the bottom layers of the stackable device creating a hypoxic environment and affecting cell viability and function. Therefore, the effect of multi-layer arrangement on oxygen distribution, dissolution in media, and utilization by cells on different layers was modeled using COMSOL4.3a (Comsol Inc., Burlington, MA). The modeling was used to understand relation between number of layers, number of cells on each layers, and depth at which oxygen concentration reaches to a level considered as hypoxic to the cells. For the simulation, 3 layers with thickness each layer 0.1 mm and 50000 cells on it. These layers are arranged at 2, 4, 6 mm from the bottom, in a well of the 12 well plate tissue culture plate. A cross section a the cylindrical well of a 12 well plate with a radius (r) of 11 mm and filled up to a height (h) of 10 mm with a cell culture media was used as a modeling geometry as depicted in FIG. 16A. Then, the oxygen consumption reaction rate "R" (mol/$M^3$·Second) of each layer with cell density "Cd" was calculated using Michaelis-Menten kinetics and the following parameters: 1) three layers with cultured chondrocytes (50,000 to 400,000 cells per layer), 2) cell culture media with glucose concentration of 2.5 g/L (25 mM) up to a height of 10 mm, and 3) maximum oxygen consumption rate ($OCR_{max}$) of 6.25× $10^{-17}$ mol/cell/second. The cell density Cd (1.315×$10^{10}$ to 10.53×$10^{10}$ cell/$m^3$) was calculated by taking the ratio of cells on one layer and the volume of culture media in the well ($\pi r^2 h$). The oxygen concentration along the vertical axis of a well in a 12 well plate is shown in FIG. 16B. COMSOL modeling in FIG. 16B shows that the concentration of oxygen from the top to bottom of well is decreased with increase in the number of cells on each layer. Oxygen concentration from top to bottom in a well with 3 layers and 50,000 cells (blue line with 1.31×$10^{10}$ cell/$m^3$) on each layer which we used in our studies is in the range far away from hypoxic conditions and each layer experiences minute variation in oxygen concentration. However, as the cell density increases not only the oxygen concentration experienced by top and bottom layer is different, but also increases the concentration difference experienced by the above layer compared to the layer below. Based on this modeling, a predication may be that if the density of cell on each layer remains constant then the oxygen concentration will decrease from the top to bottom with an increase in number of layers. In this way, modeling suggests that the selection of number of layers and cells on each layer are essential parameters to culture the cells in such stacking arrangement without limiting the oxygen to layers below the top.

Example 3

Membrane coating testing and characterization. As a first step, the ability of the membranes to be coated with functional molecules that could promote cell attachment and function was tested.

Figure 6B:
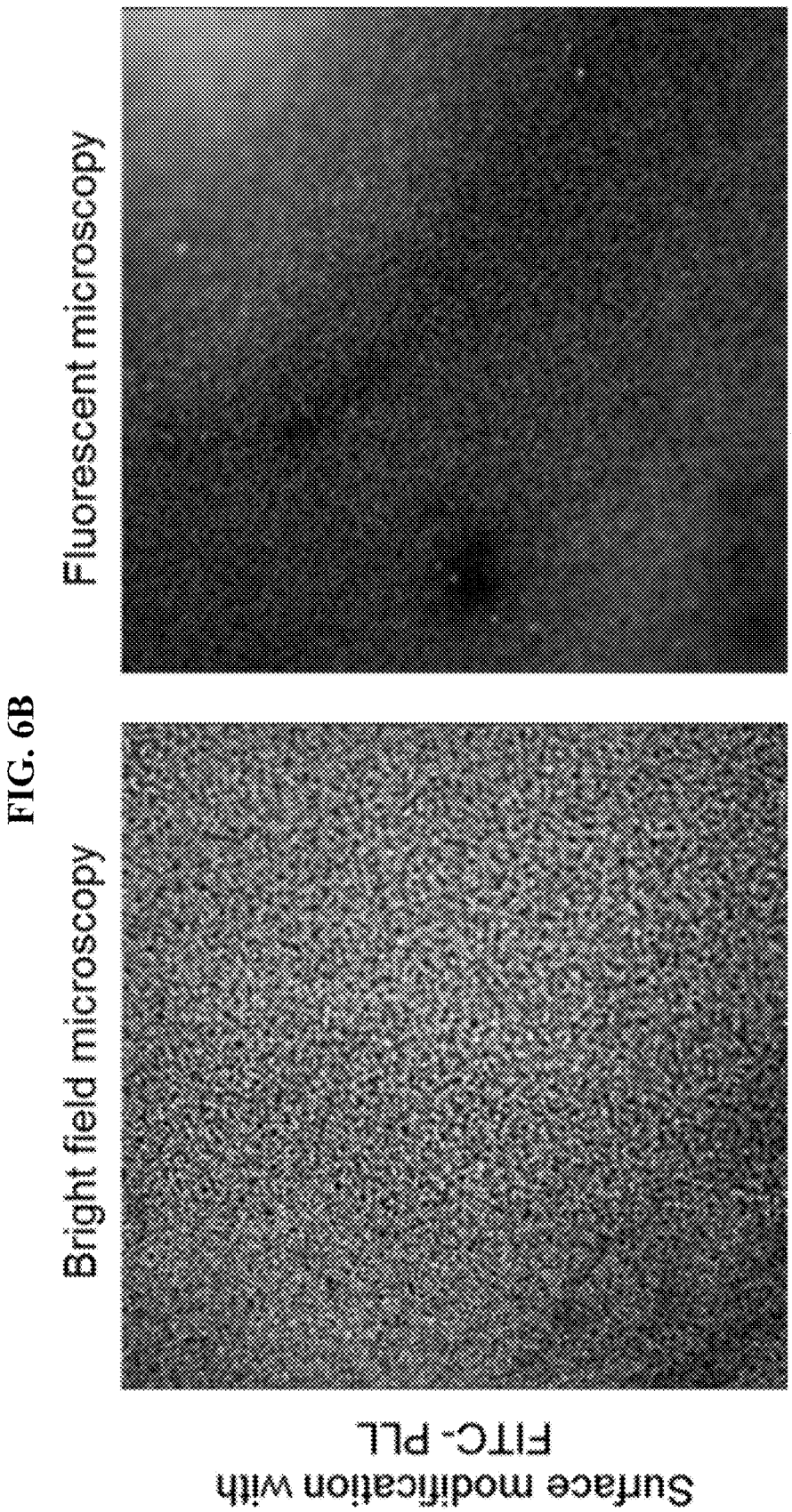
FIG. 6 shows microscopy images illustrating a comparison of membrane surface coating. The microporous membrane can be uncoated (FIG. 6A) or coated and/or modified with different materials (FIG. 6B, FIT-C PLL) to provide mechanical and three dimensional cues to recreate the native environment of the cell.

Surface coating: As an initial test molecule, the microporous membrane was coated with FIT-C labeled Poly-L-Lysine (PLL) and then observed by fluorescence microscopy to detect binding of the polyamino acid to the membrane. Membranes coated with FITC-PLL (FIG. 5B and FIG. 6B) have a fluorescent signal and the fibers of the membrane can be seen coated with FITC-PLL; while non-coated membrane have only background signal (FIG. 6A and FIG. 6B).

Figure 7A:
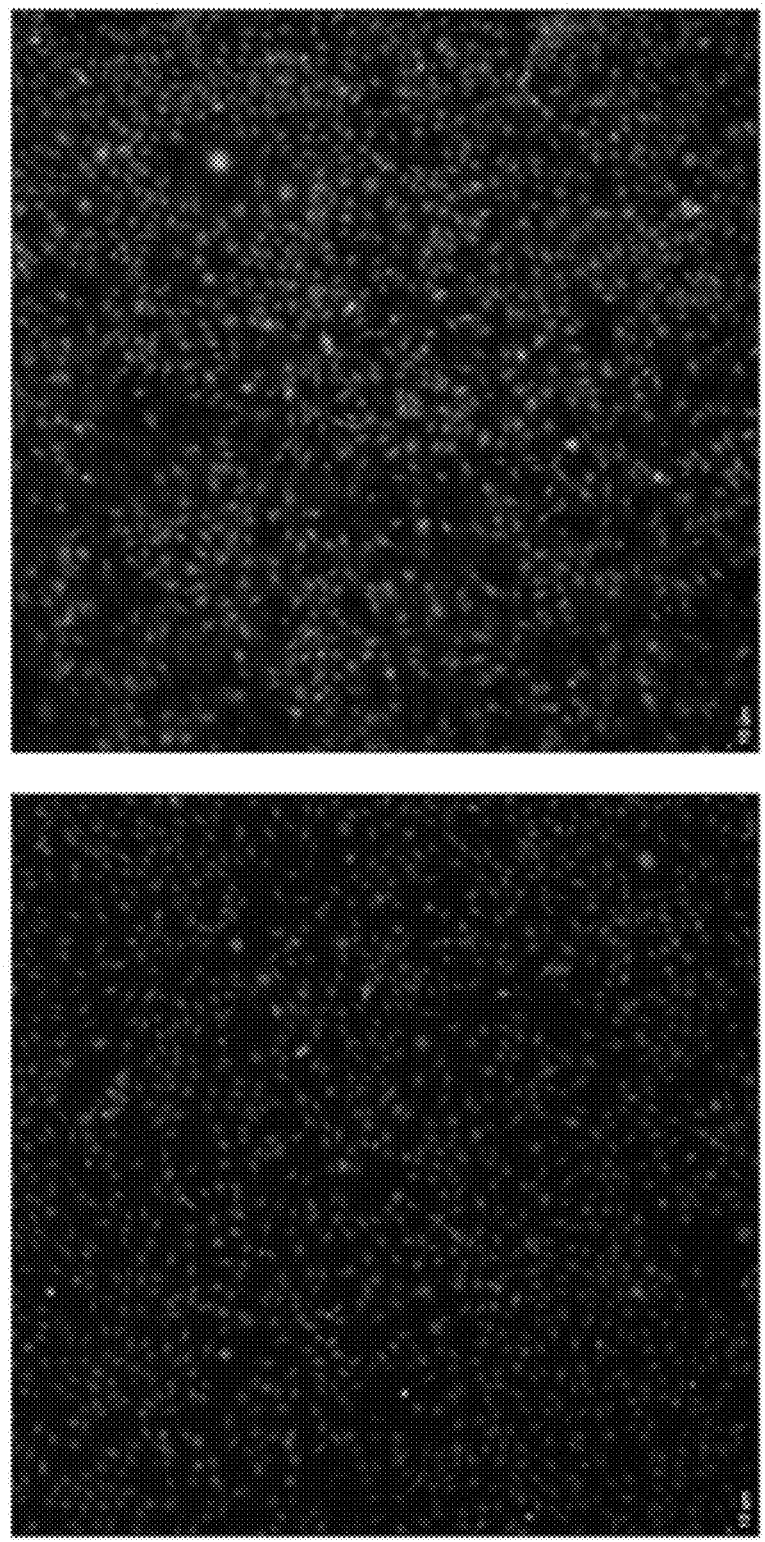
FIG. 7 shows representative images of human chondrocytes after 48 hours of culture on uncoated tissue culture plastic or microporous membrane (FIG. 7A) and coated tissue culture plastic or microporous membrane (FIG. 7B).
Figure 7B:
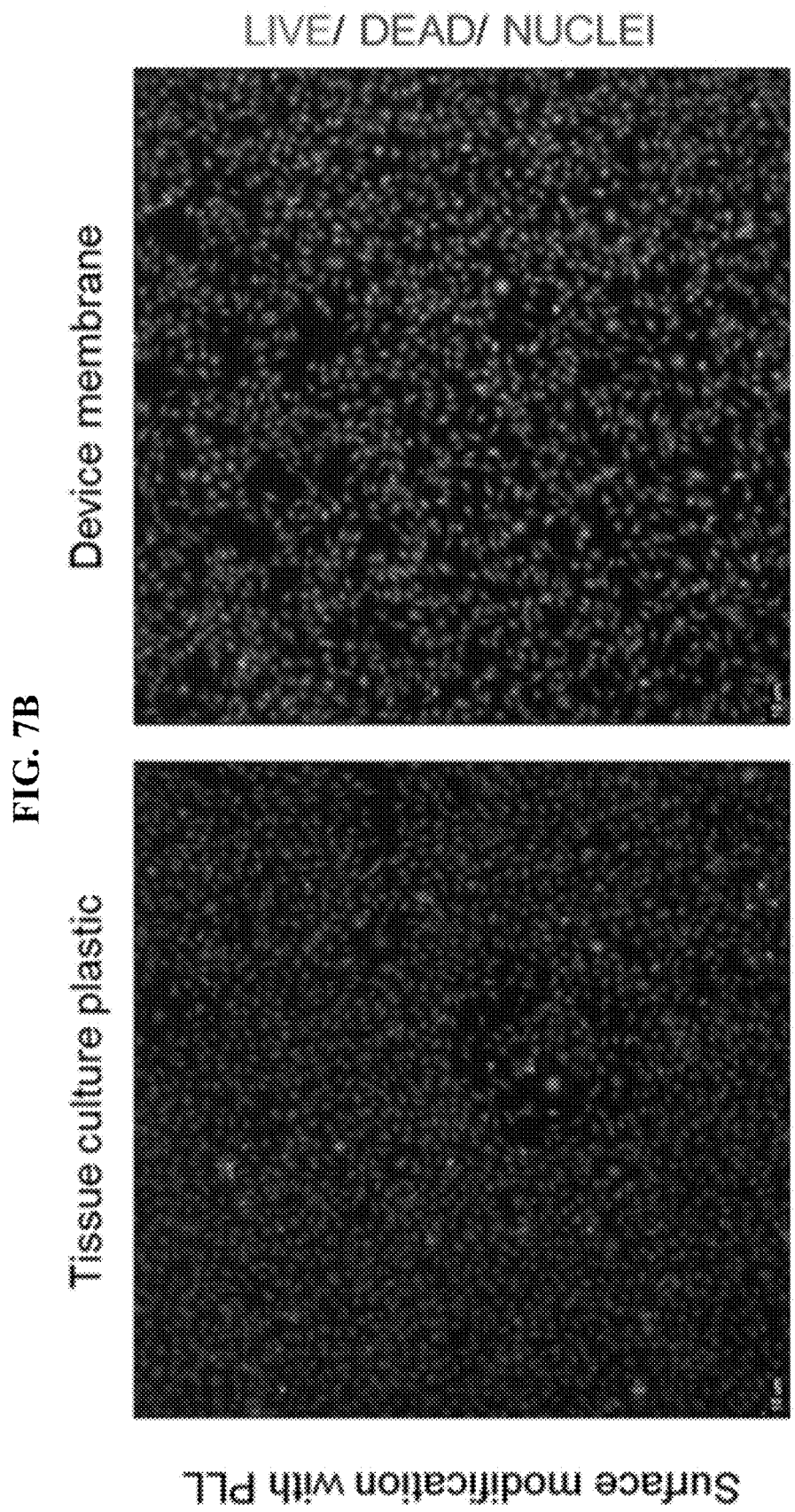
Figure 8A:
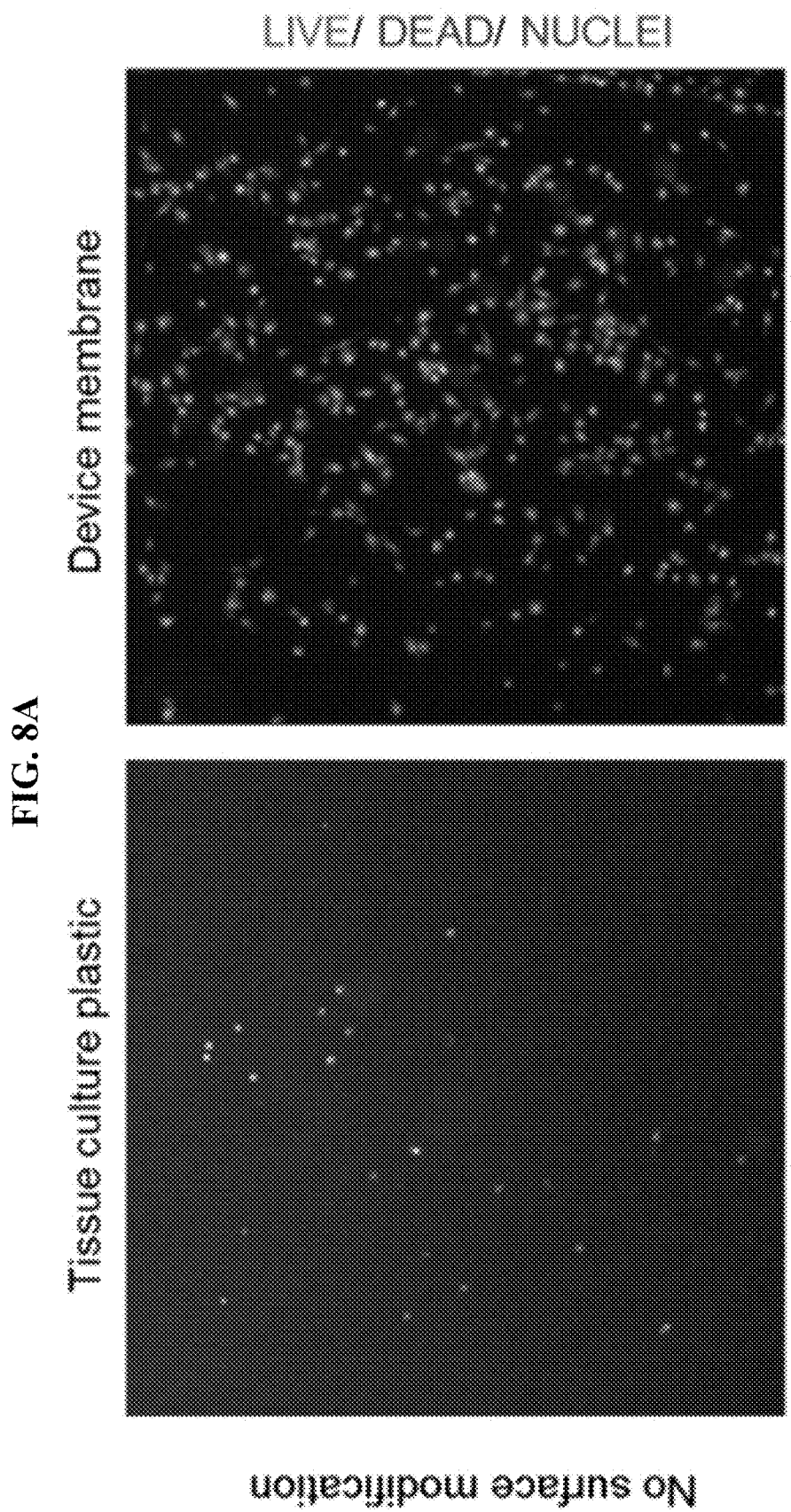
FIG. 8 shows representative images of macrophages after 48 hours of culture on uncoated tissue culture plastic or microporous membrane (FIG. 8A) and coated tissue culture plastic or microporous membrane (FIG. 8B).
Figure 8B:
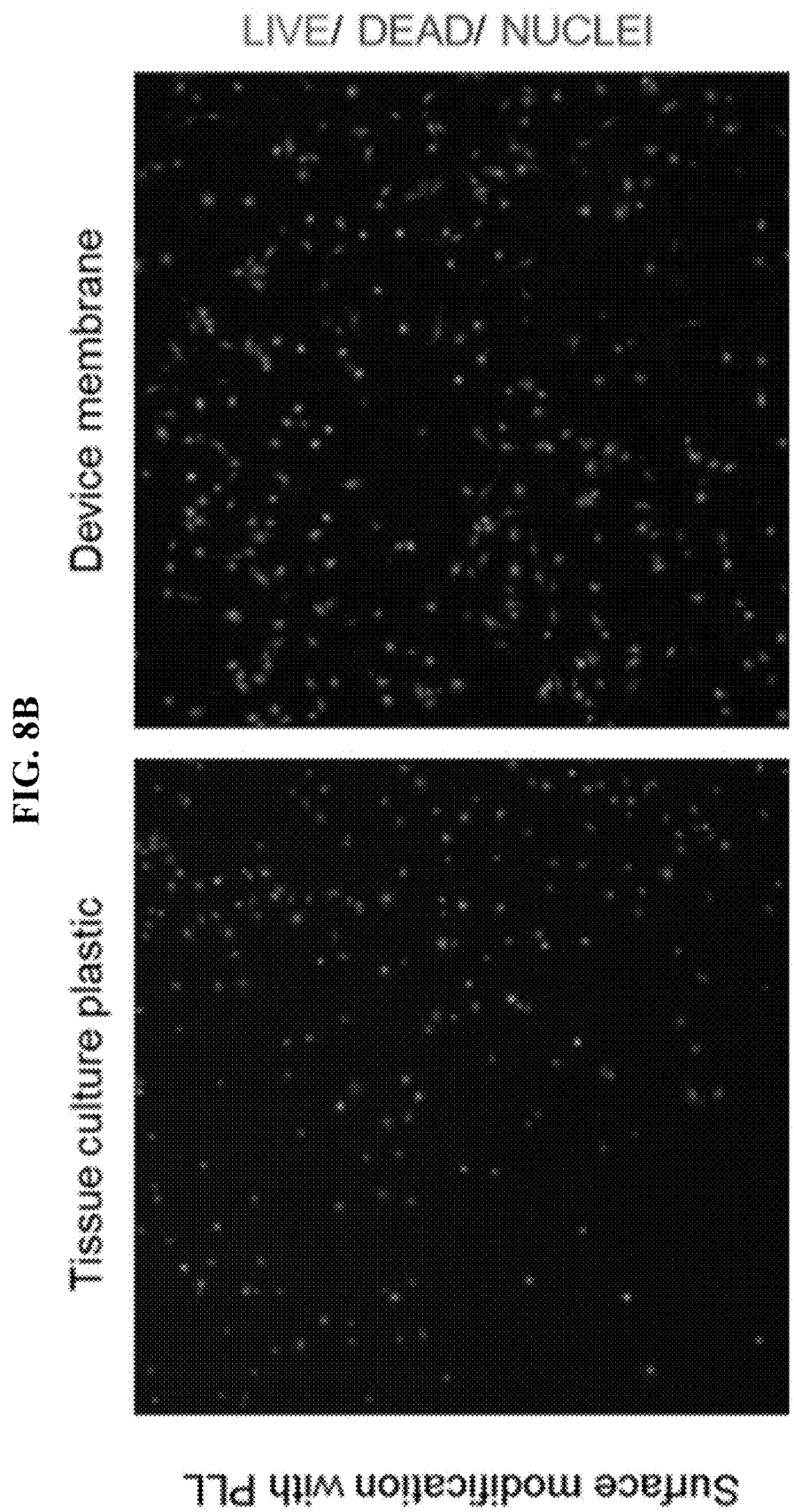
Figure 9A:
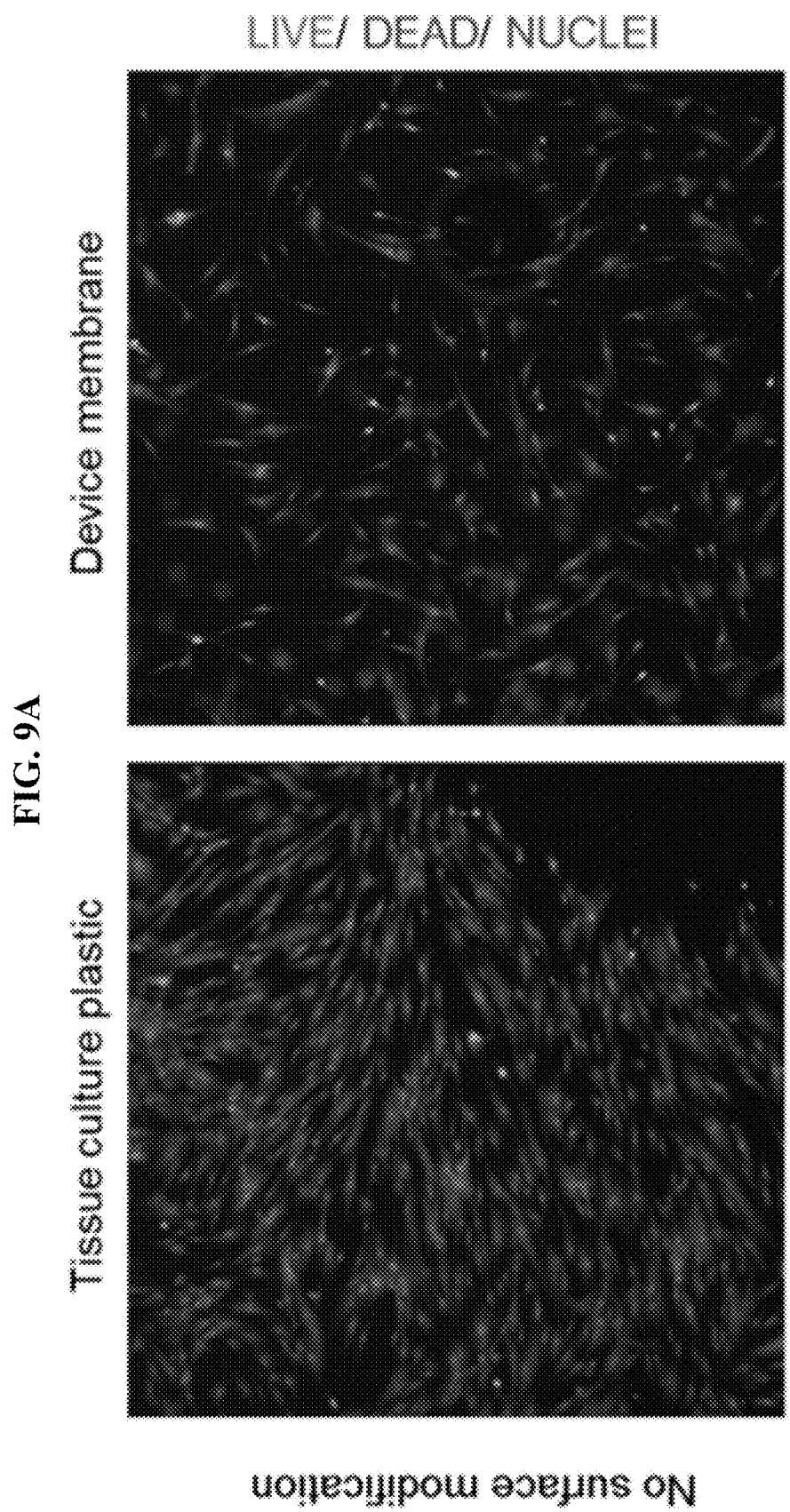
FIG. 9 shows representative images of mesenchymal stromal cells (MSC) after 48 hours of culture on uncoated tissue culture plastic or microporous membrane (FIG. 9A) and coated tissue culture plastic or microporous membrane (FIG. 9B).
Figure 9B:
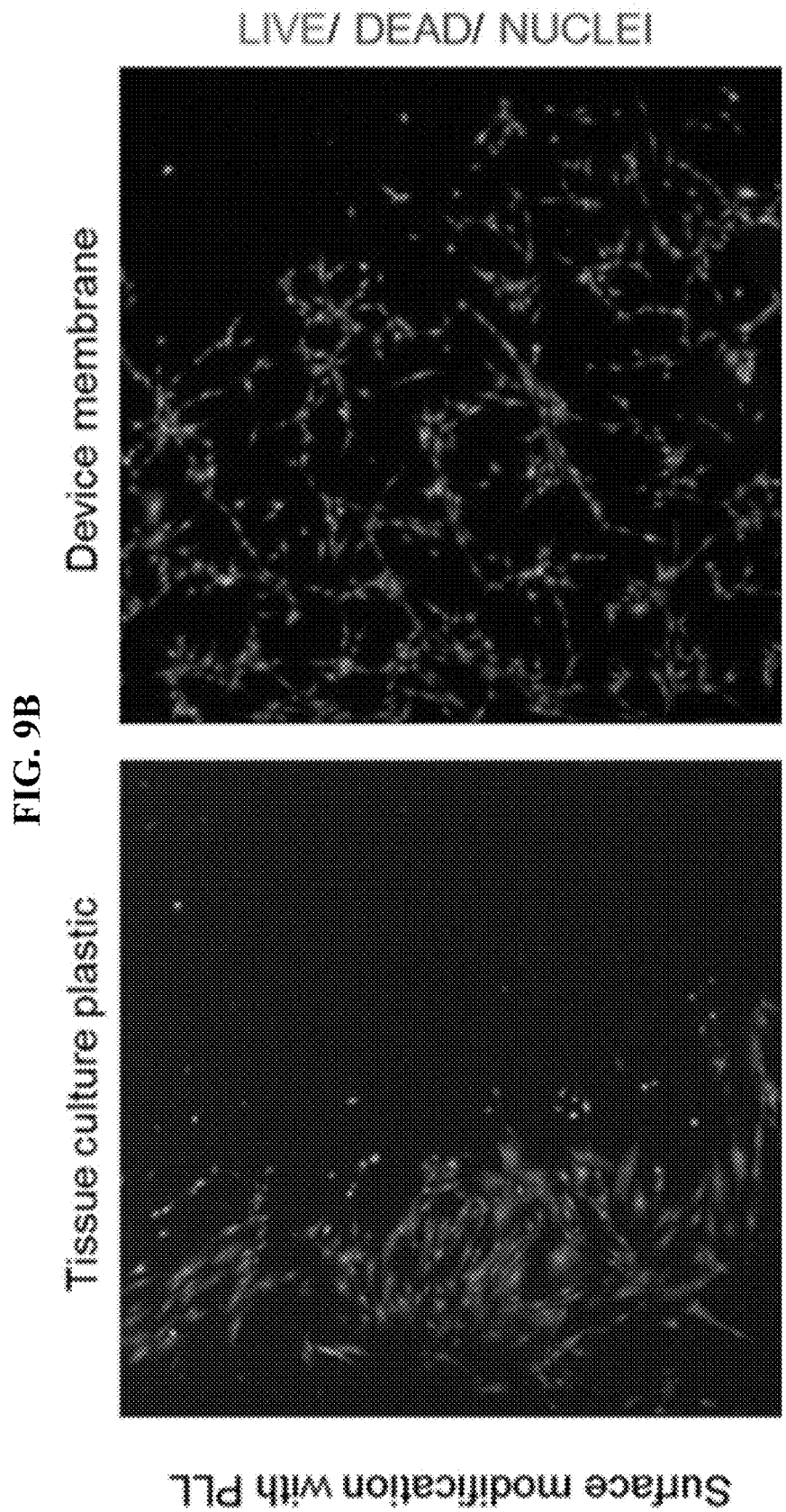

Cell seeding: Next, each of the cell types was seeded in separate device compartments. Chondrocytes, macrophages, and MSC were seeded in the stackable insert to begin to characterize the cell attachment, viability, and function of different cell types with this device. For this, 95,000 cells were seeded in 12 well plates alone (3.8 cm$^2$ growth area) or containing the stackable insert with and without PLL coating (1.82 cm$^2$ growth area) or transwell inserts (0.9 cm$^2$ growth area) (Corning). Cells seeded in tissue culture treated plastic with and without PLL coating were used as a control. After 48 hours, the cells were stained with calcein AM, ethidium homodimer, and Hoechst to differentiate live cells, dead cells, and nuclei, respectively and visualized at 4× using an inverted fluorescent microscope. Overall, viable cell attachment was observed for all the cell types (FIGS. 6-8). PLL coating had no major effect on cell attachment and viability for the chondrocytes; on the other hand it promoted cell attachment for the macrophages and MSC (FIGS. 7-9).

Figure 10A:
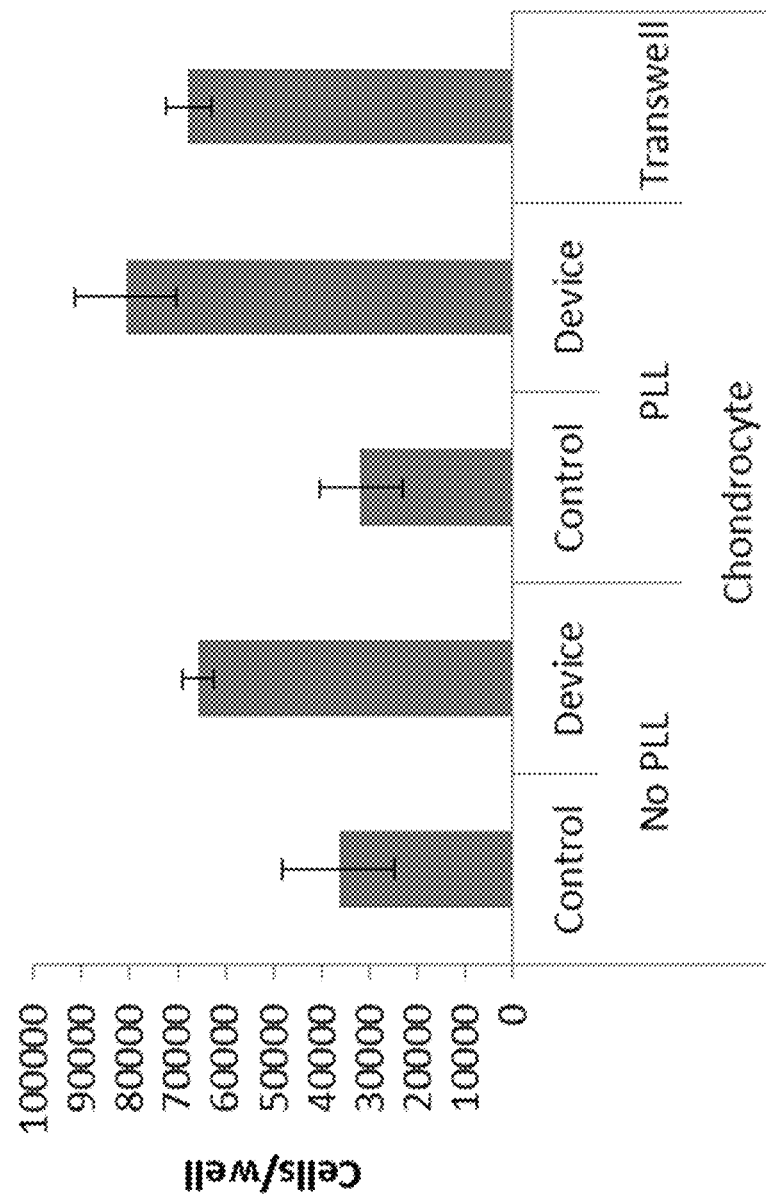
FIG. 10A, FIG. 10B, and FIG. 10C show the number of attached chondrocytes (FIG. 10A), macrophages (FIG. 10B) and mesenchymal stromal cells (FIG. 10C) after 48 hours in culture (n=3 biological replicates per condition).
Figure 10B:
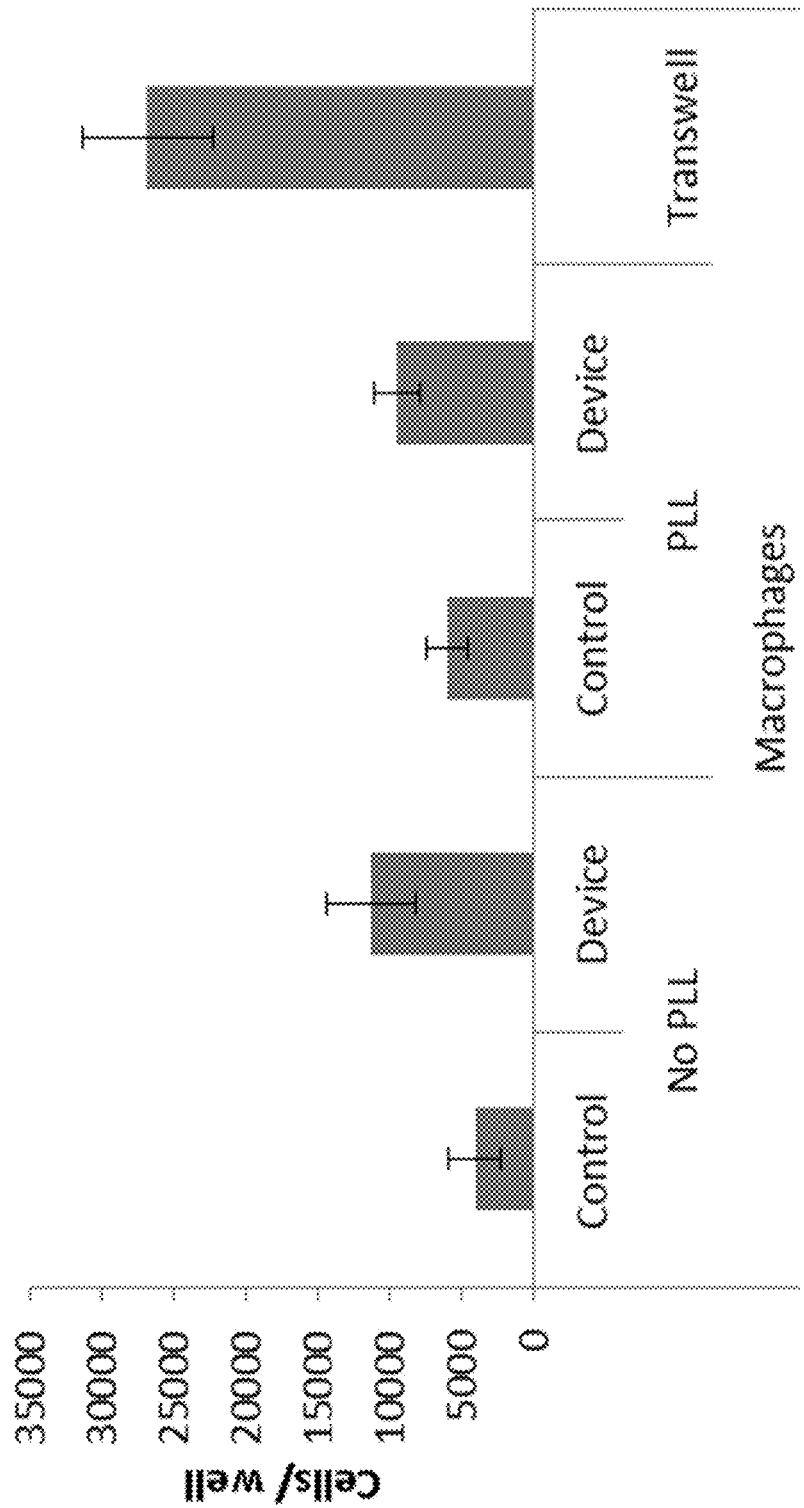
Figure 10C:
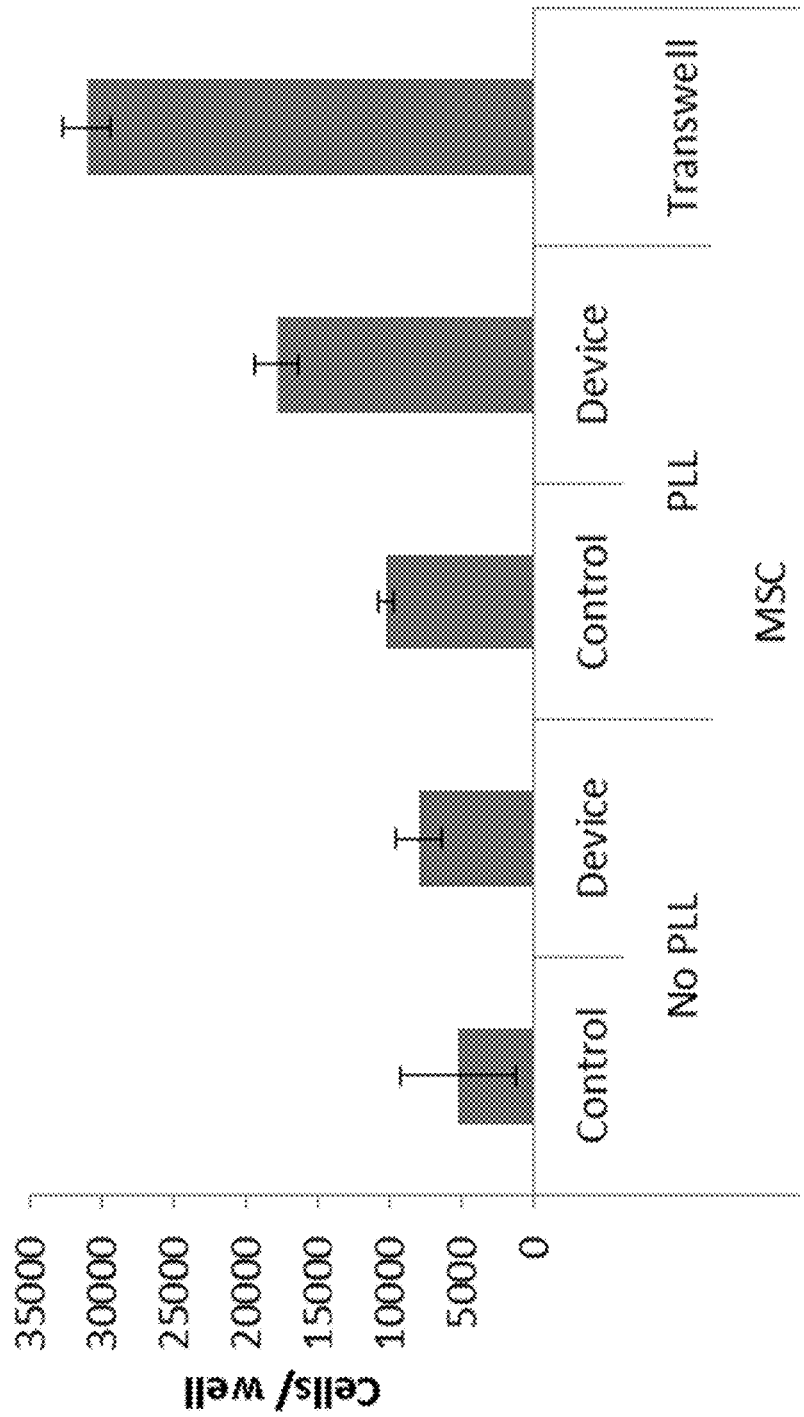
Figure 11A:
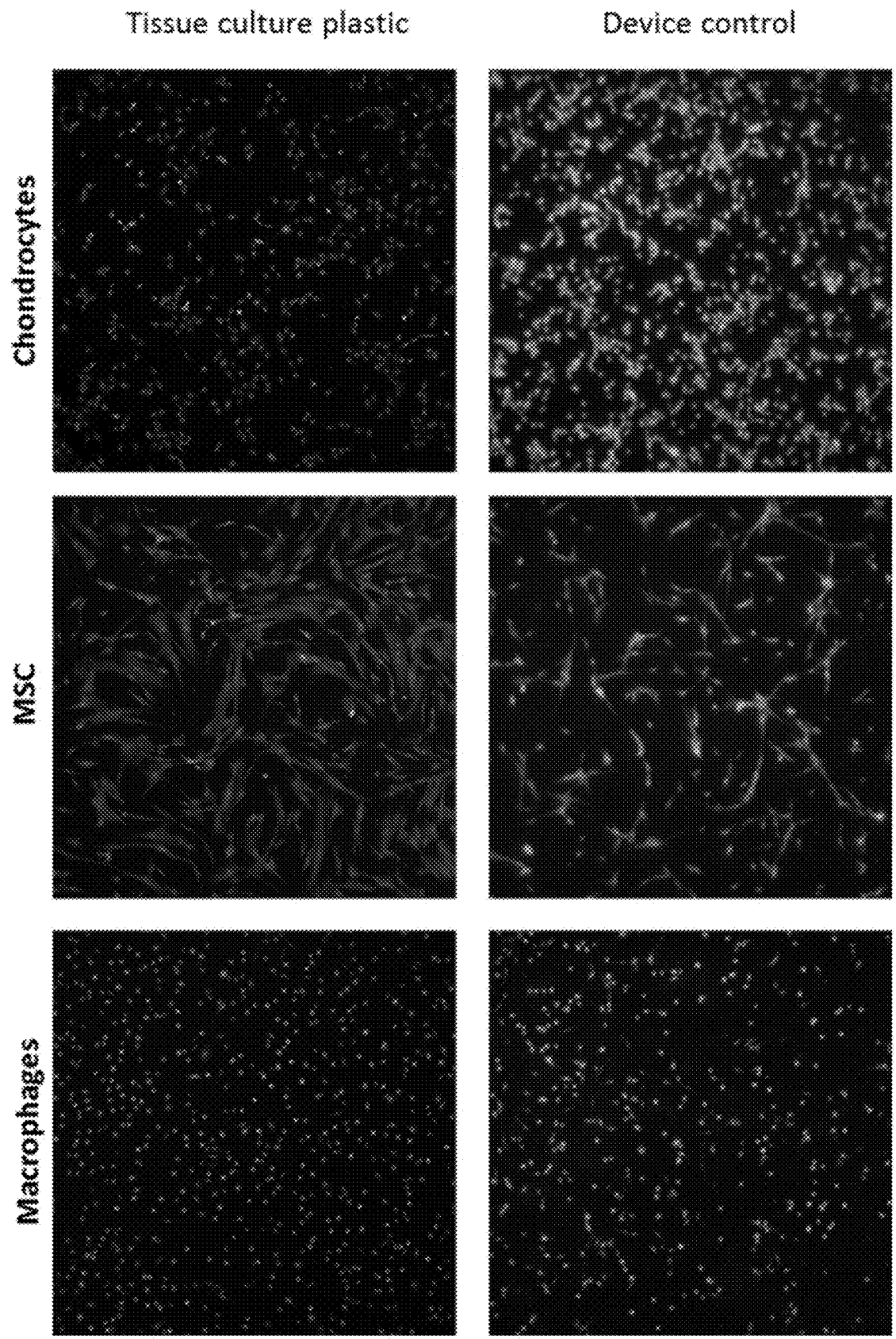
FIG. 11A shows tissue culture plastic and device control conditions.
Figure 11B:
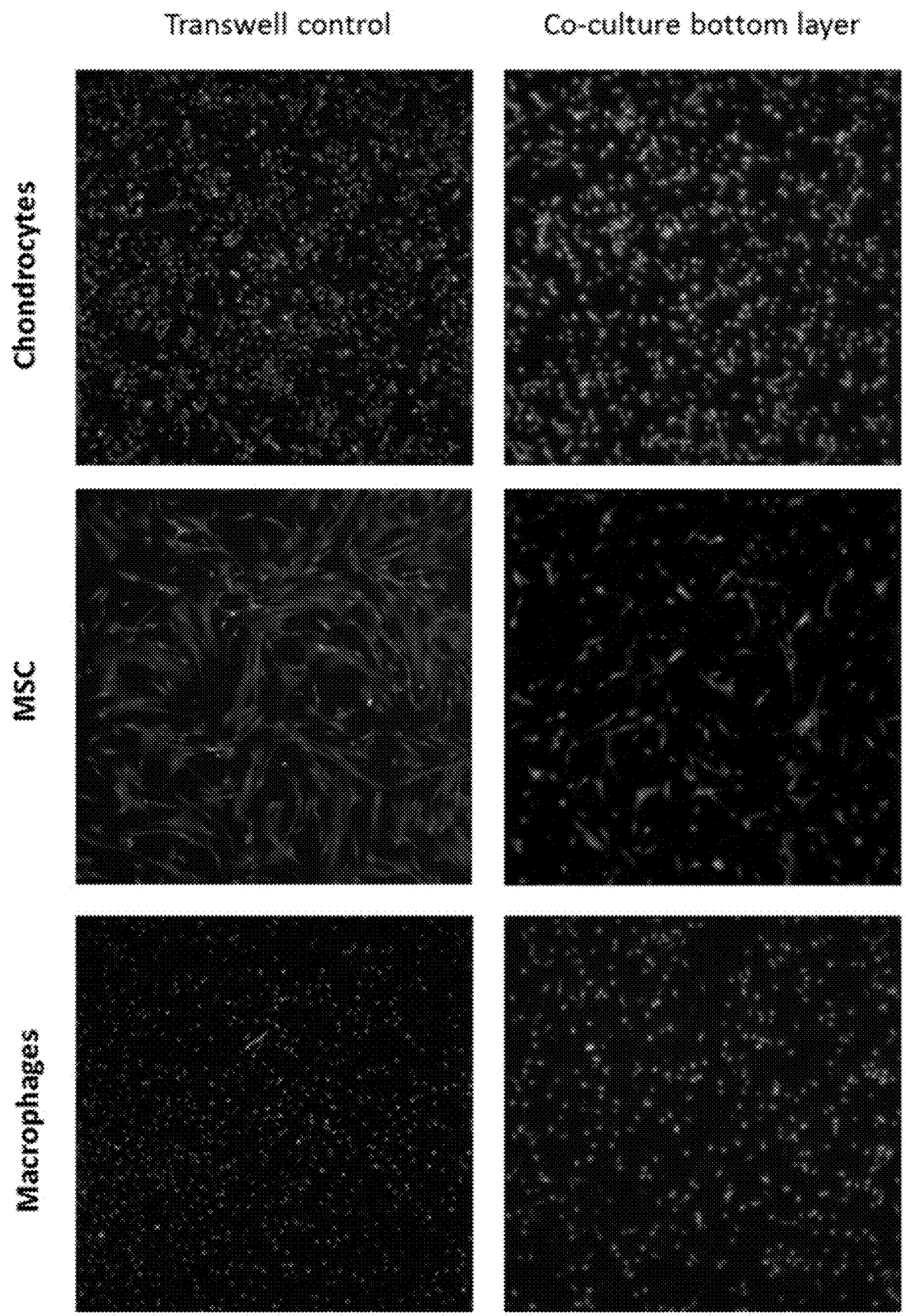
FIG. 11B shows transwell control and co-culture bottom layer conditions.
Figure 11C:
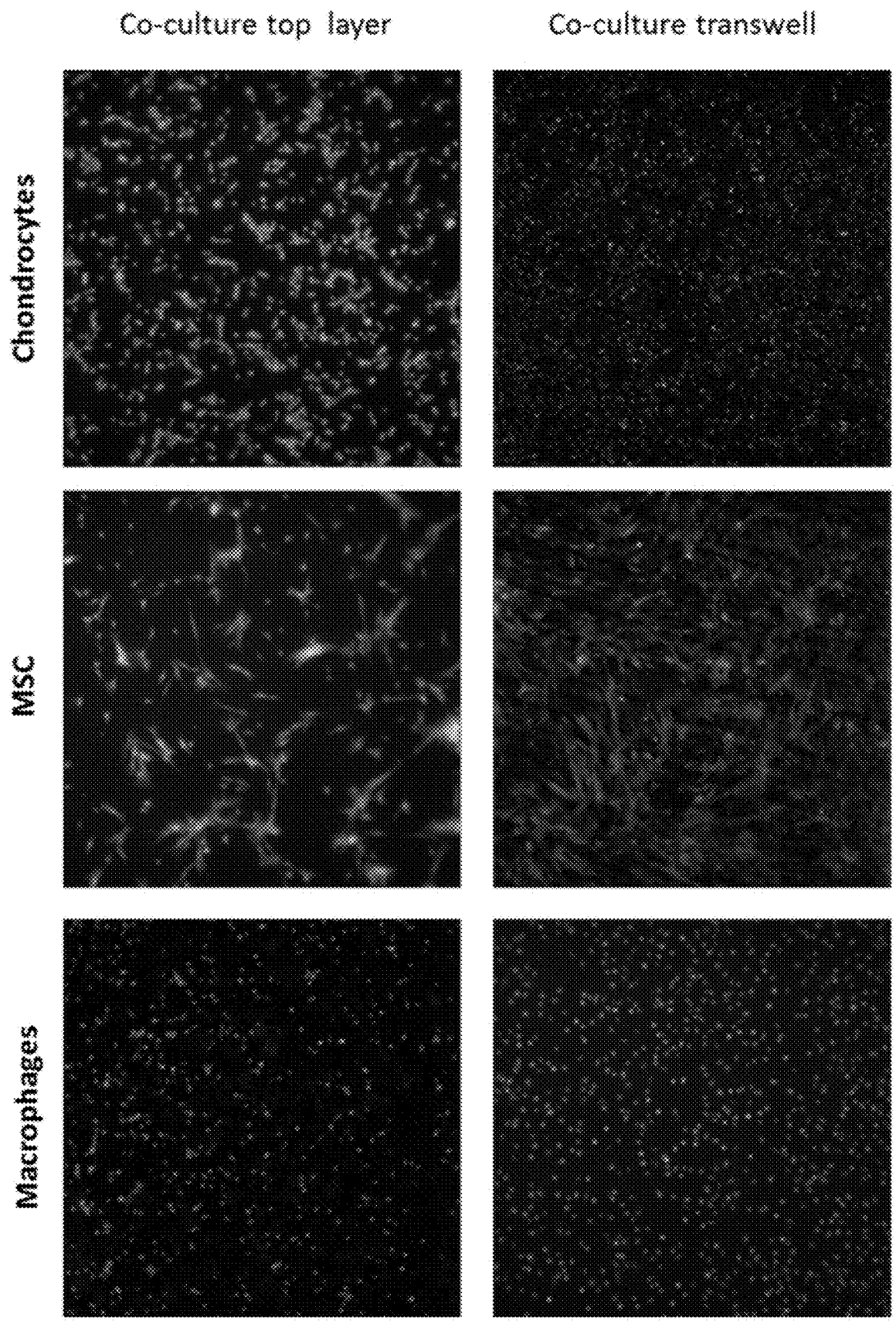
FIG. 11C shows co-culture top layer and co-culture transwell conditions.
Figure 11D:
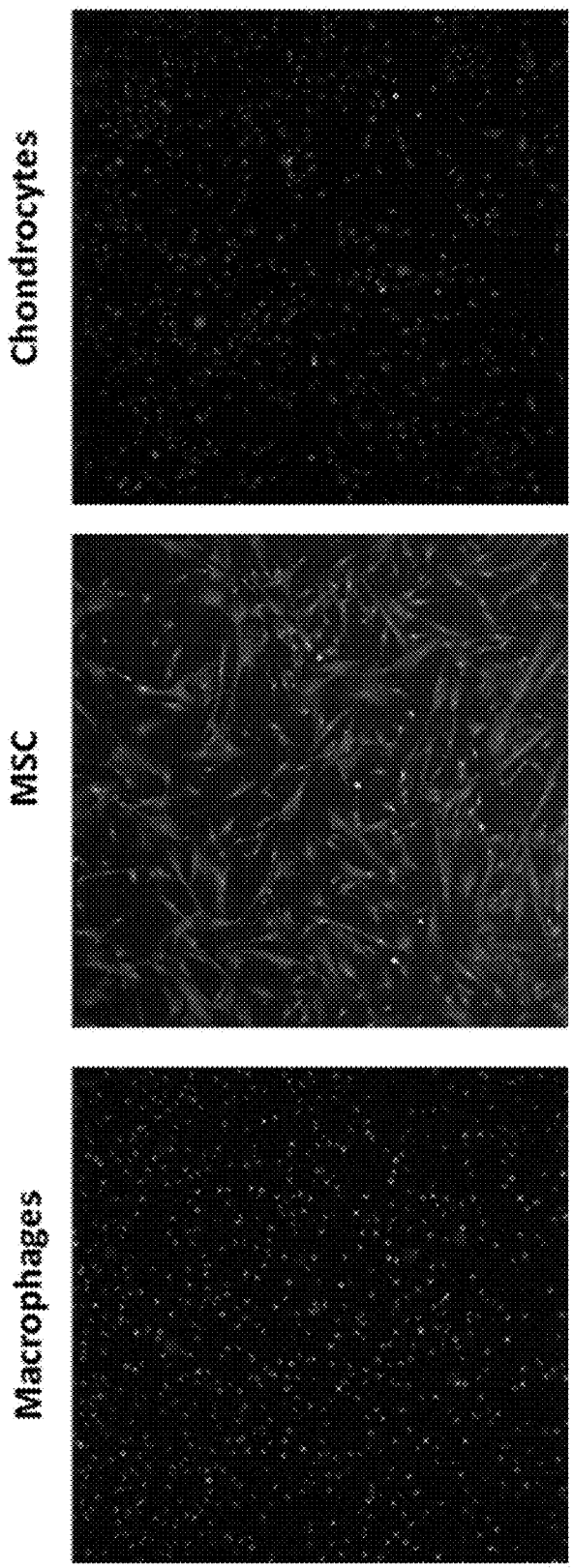
FIG. 11D shows the co-culture transwell bottom well condition.

Stained nuclei were counted using ImageJ software to determine cell attachment number. Overall there were no statistically significant differences in cell attachment (nuclei number) between the tissue culture plate and the device's membrane (FIG. 10).

Example 4

Multilayer Stackable Tissue Culture Platform for 3D Co-Culture. The technology disclosed herein advances the recreation of native tissue like arrangements of different types of cells in an in vitro cell culture model to improve the accuracy of the studies using such in vitro systems. Individual types of cells were cultured separately on each stack and then arranged together inside the well to establish the multi-layer 3D co-culture.

Cell seeding: Chondrocytes, macrophages, and MSC were seeded in the stackable insert to begin to characterize the cell attachment, viability, and function of different cell types with this device. For this, cells were seeded at a concentration of 25,000 cells/cm$^2$ in 12 well plates alone (3.8 cm$^2$ growth area) or containing the stackable insert (1.82 cm$^2$ growth area) with PLL coating or transwells (0.9 cm$^2$ growth area). The cells were incubated overnight at 37° C., 5% $CO_2$ to let them attach. Then, MSCs or macrophages were placed on co-culture with chondrocytes for 48 hours at 37° C., 5% $CO_2$. The cells were stained with calcein AM, ethidium homodimer, and Hoechst to differentiate live cells, dead cells, and nuclei, respectively and visualized at 4× using an inverted fluorescent microscope. Overall, viable cell attachment was observed for all cell types (FIG. 11).

Figure 13:
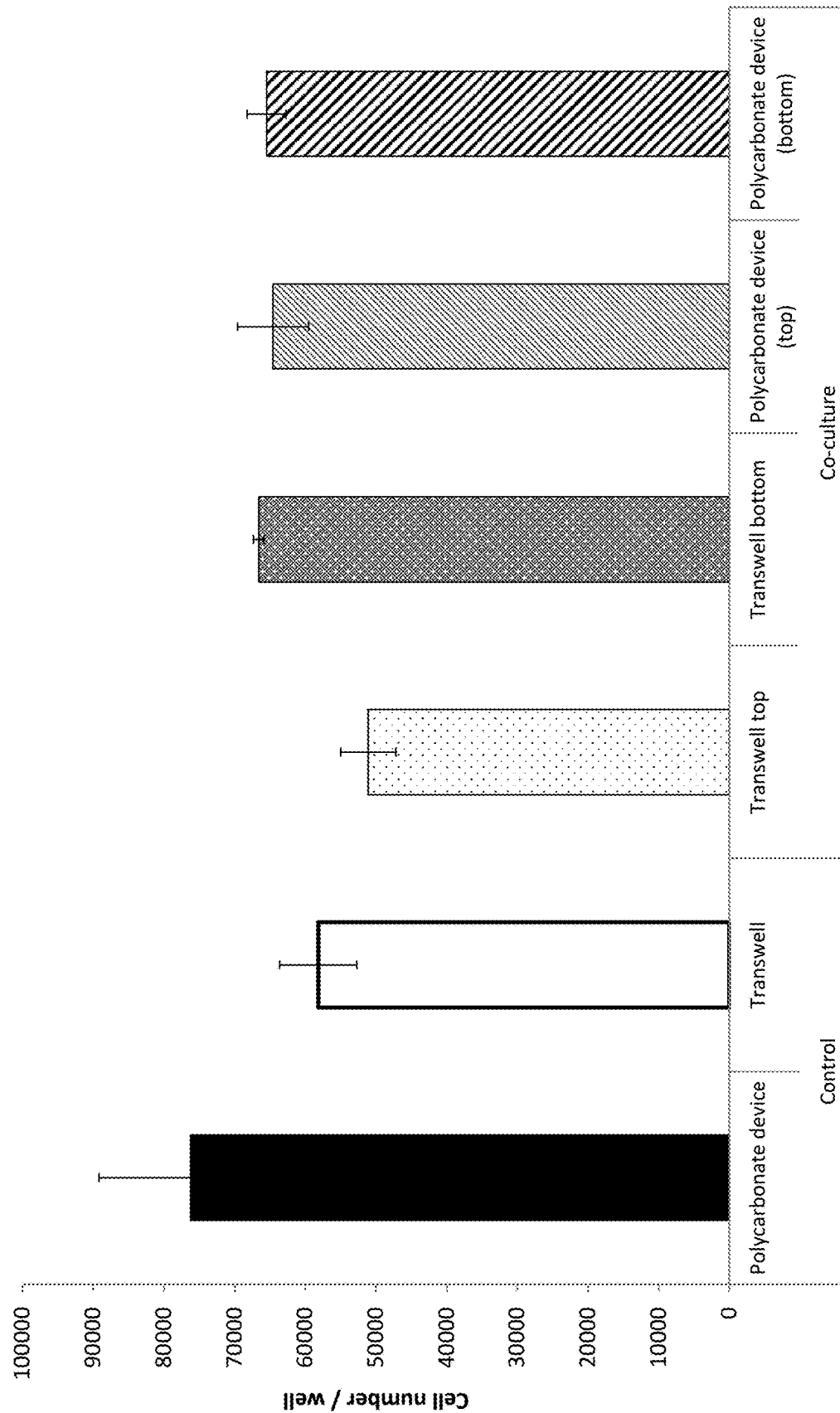
FIG. 13 is a bar graph showing chondrocyte cell number per well in co-culture or single culture with macrophages or mesenchymal stromal cells.
Figure 14:
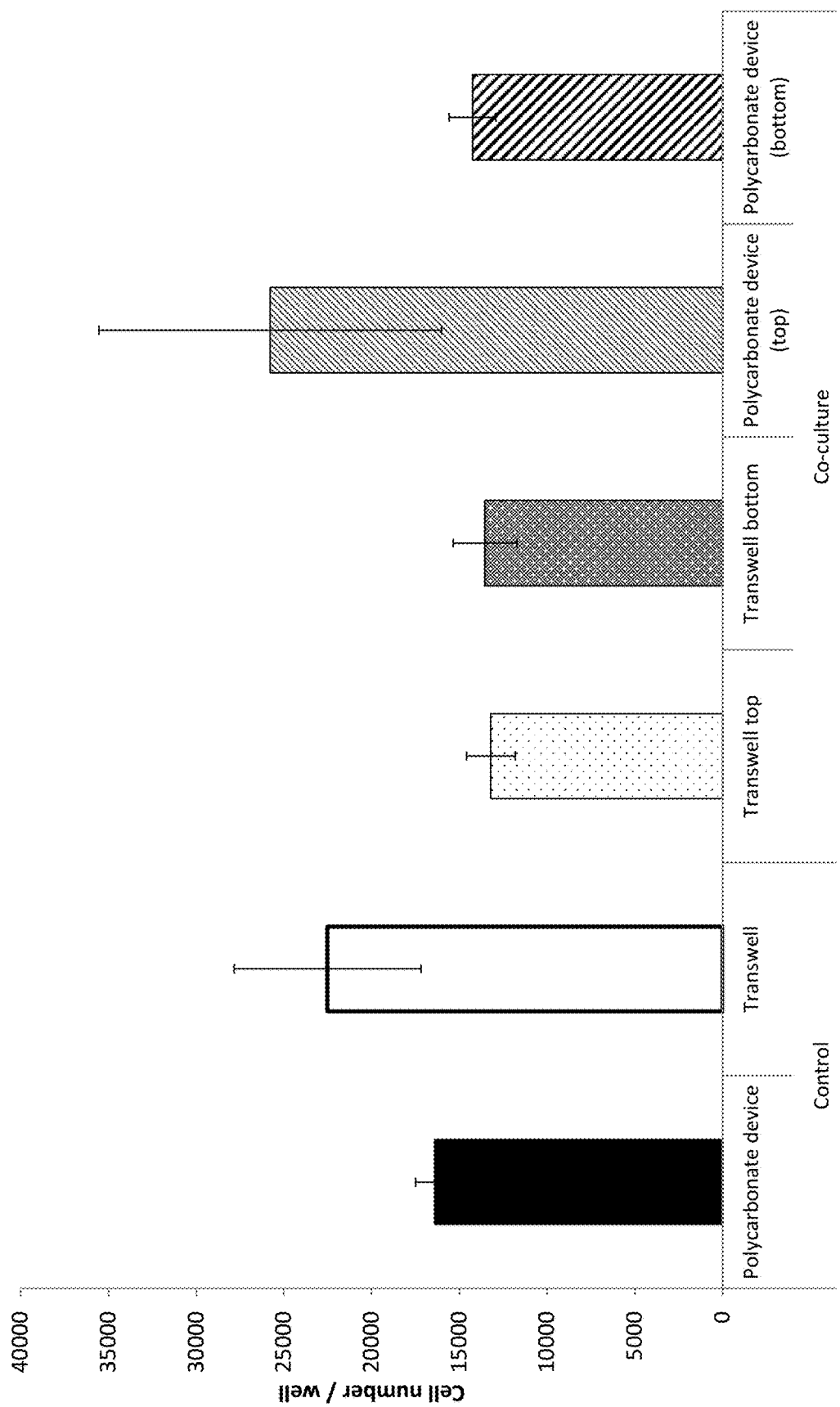
FIG. 14 is a bar graph showing macrophage cell number per well in co-culture or single culture with chondrocytes.
Figure 15A:
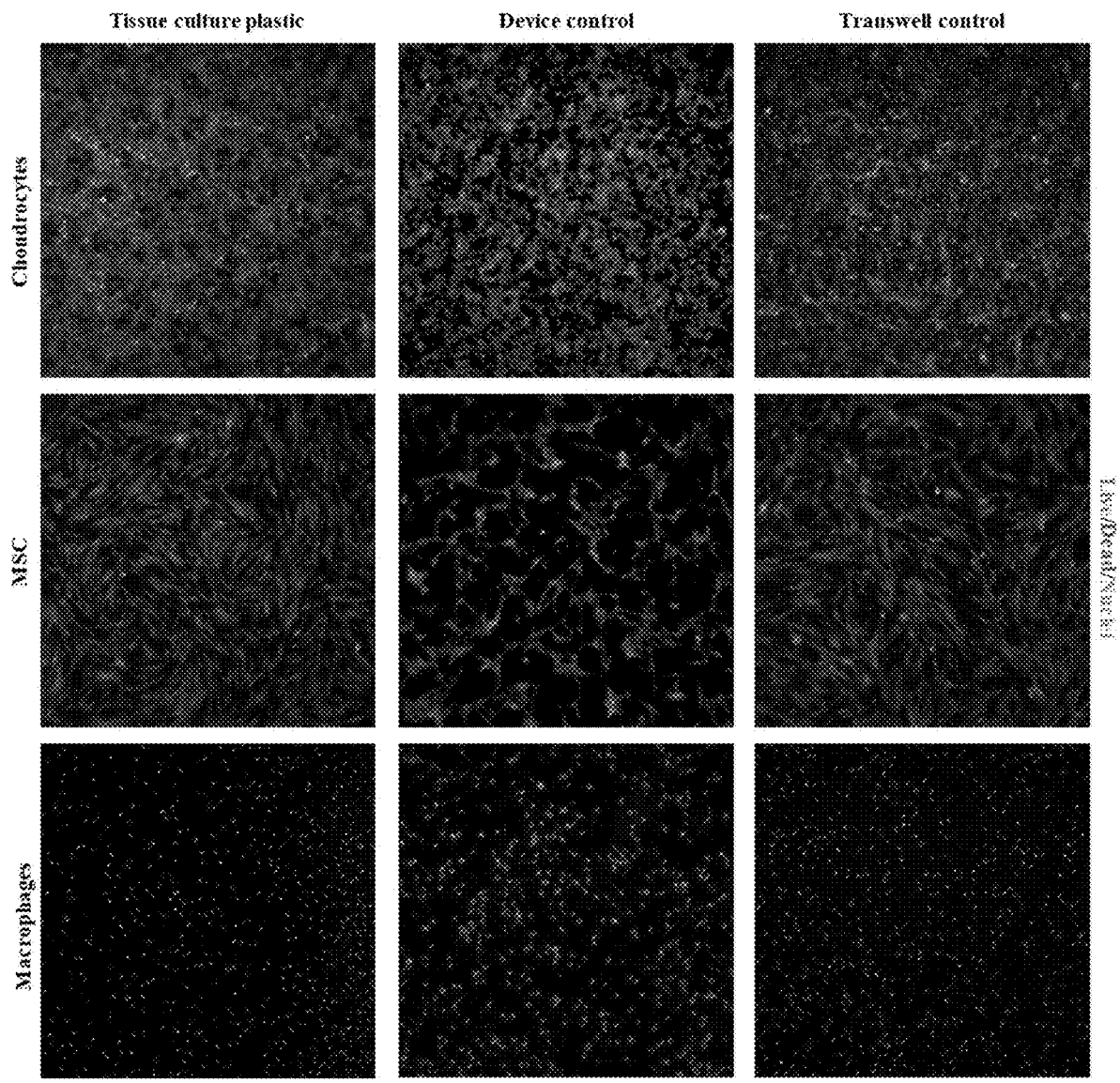
FIG. 15A shows representative images of cells seeded in the stackable tissue culture insert, TCPS well, or transwell inserts. Percentage of viable chondrocytes (FIG. 15B), macrophages (FIG. 15C), and MSC (FIG. 15D) in all growth substrates. The minimum viability values were 98%, 94% and 84% for chondrocytes, macrophages, and MSC, respectively when seeded in the stackable insert. Bar graphs represent the average percent viability (%)±SEM of n=8-24 images for at least 2 independent experiments (P<0.05 as compared to Well (*), Device (#), or Transwell (+) by ANOVA with Fisher's LSD post hoc test). NS=not significant.
Figure 15B:
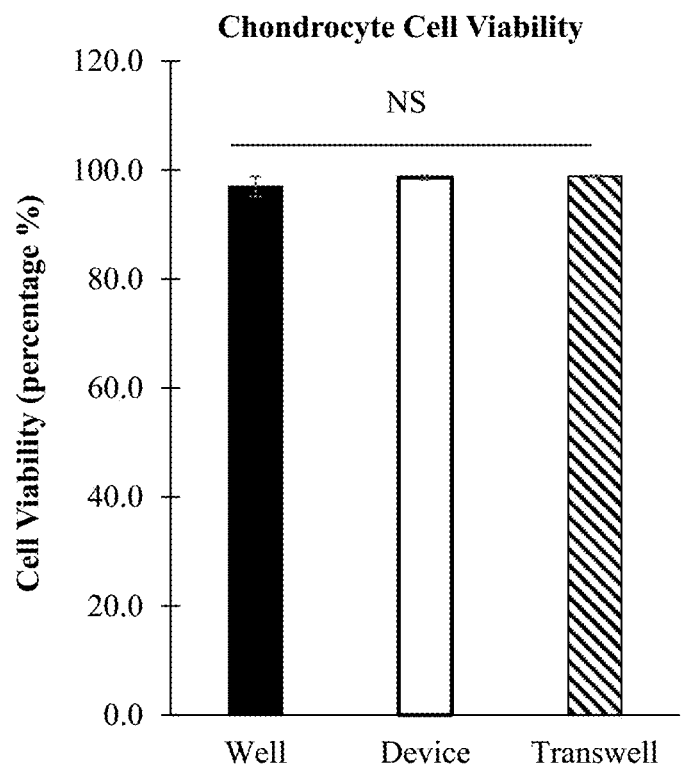
FIG. 15 shows cell viability comparison.
Figure 15C:
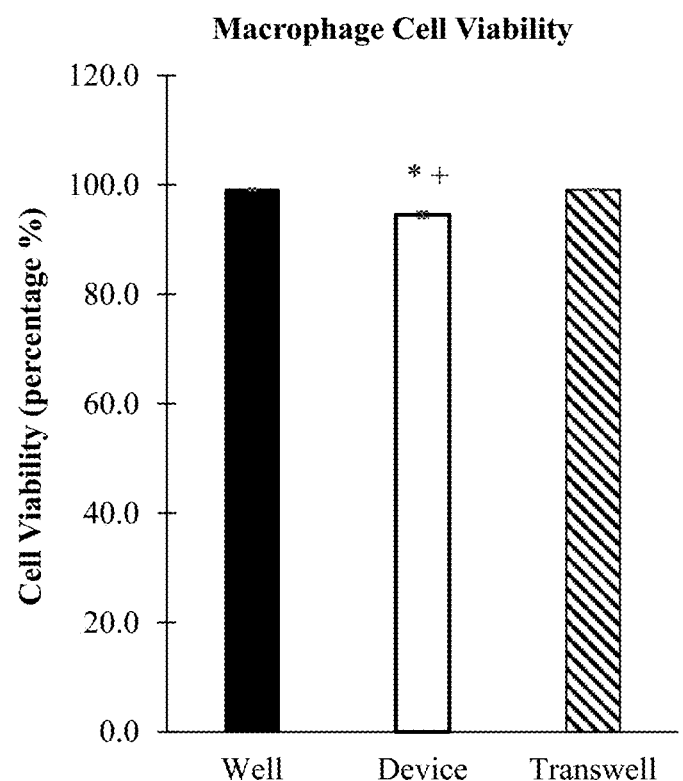
Figure 15D:
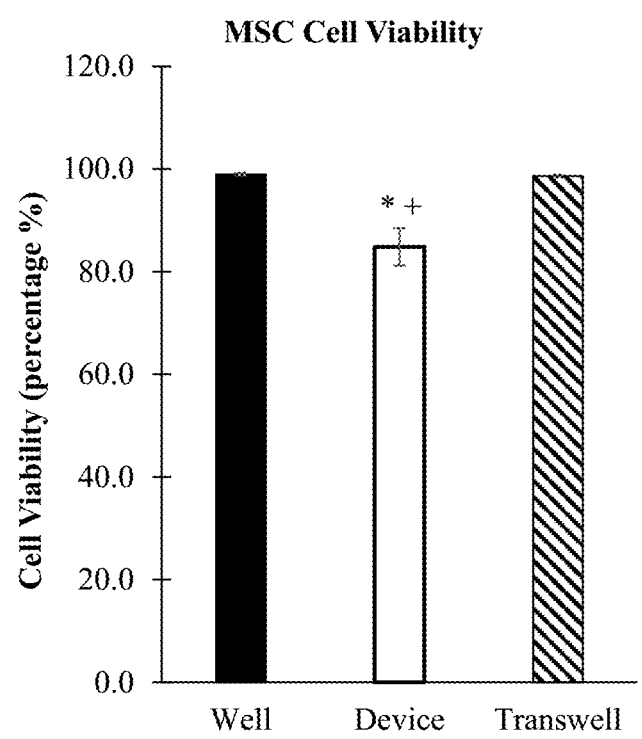

Stained nuclei were counted using ImageJ software to determine cell attachment number. Overall attachment per growth area remained constant for cells when cultured alone or in co-culture independently of their substrate (stackable insert or transwell inserts) or their culture configurations (top or bottom layers) as shown in FIGS. 12-14.

Example 5

Cell Functional Secretion. Since one of our main interests by developing a stackable tissue culture insert is to study cell paracrine interactions, it was important to characterize the effects on cell secretory function. We first examined interleukin (IL)-8, a chemokine which recruits neutrophils to an injury site. IL-8 is secreted by a variety of cell types including chondrocytes, pro-inflammatory macrophages and MSCs. We compared secretion levels on all cell types with standard tissue culture and transwells. In our studies we found that IL-8 was secreted by all cell types. However, macrophages had the highest secretion levels when cultured on all substrates, followed by chondrocytes and then MSC (FIG. 17). Interestingly, IL-8 secretion values were comparable between the cells cultured on TCP and the stackable inserts, while cells seeded on transwell inserts had significantly lower secretion levels.

IL-6 secretion was also measured, since this pleiotropic cytokine has been found to be constitutively secreted by chondrocytes (in low levels) and MSC, and secreted by macrophages when exposed to inflammatory stimuli. As indicated by FIG. 17, IL-6 total secretion levels vary depending on the cell type, where MSC secreted more IL-6 when cultured on all substrates, followed by chondrocytes, and no secretion was detected in the macrophage supernatants. In addition, there was no significant difference in the level of IL-6 secreted by each cell type when comparing the stackable insert and transwell inserts.

Finally, tumor necrosis factor (TNF-) α levels were assessed by ELISA. TNF-α is a well described pro-inflammatory cytokine secreted by osteoarthritic chondrocytes and classically activated macrophages in the presence of inflammatory stimuli such as lipopolysaccharide (LPS). High levels of TNF-α could also indicate endotoxin contamination generated during the stackable insert fabrication and sterilization process. However, the presence of TNF-α was not detected in any of the cell types for all substrates. Collectively, these studies suggest that cytokine secretion can be substrate dependent, regardless of whether the substrates represent traditional "gold standards" such as TCP and transwells, or our novel stackable insert, further supporting the need for multi-culture substrate uniformity when developing multi-culture in vitro systems.

Multi-Culture Studies. Thus far our studies indicate that individual cell types can remain viable and maintain functional secretion in the stackable tissue culture inserts. In addition, the $O_2$ diffusion model indicated that cells will have adequate $O_2$ supply through the insert stack for a wide range of cultured cells per insert in a three insert per well configuration FIG. 16. Therefore, studies were next designed to test the efficacy of our custom inserts in a tri-culture system, including chondrocytes, macrophages, and MSC in different spatial configurations as indicated in Table 1. Cell attachment and functional secretion influenced by paracrine signaling were assessed after 48 hours in culture.

TABLE 1

Tri-culture studies stack configurations. Stackable inserts seeded with chondrocytes, macrophages, or MSC were arranged in a well following six different configurations and cultured for 48 hours.

| Configuration | 1 | 2 | 3 | 4 | 5 | 6 |
|---|---|---|---|---|---|---|
| Top | Macrophages | MSC | Macrophages | Chondrocytes | Chondrocytes | MSC |
| Middle | MSC | Macrophages | Chondrocytes | MSC | Macrophages | Chondrocytes |
| Bottom | Chondrocytes | Chondrocytes | MSC | Macrophages | MSC | Macrophages |

Figure 19A:
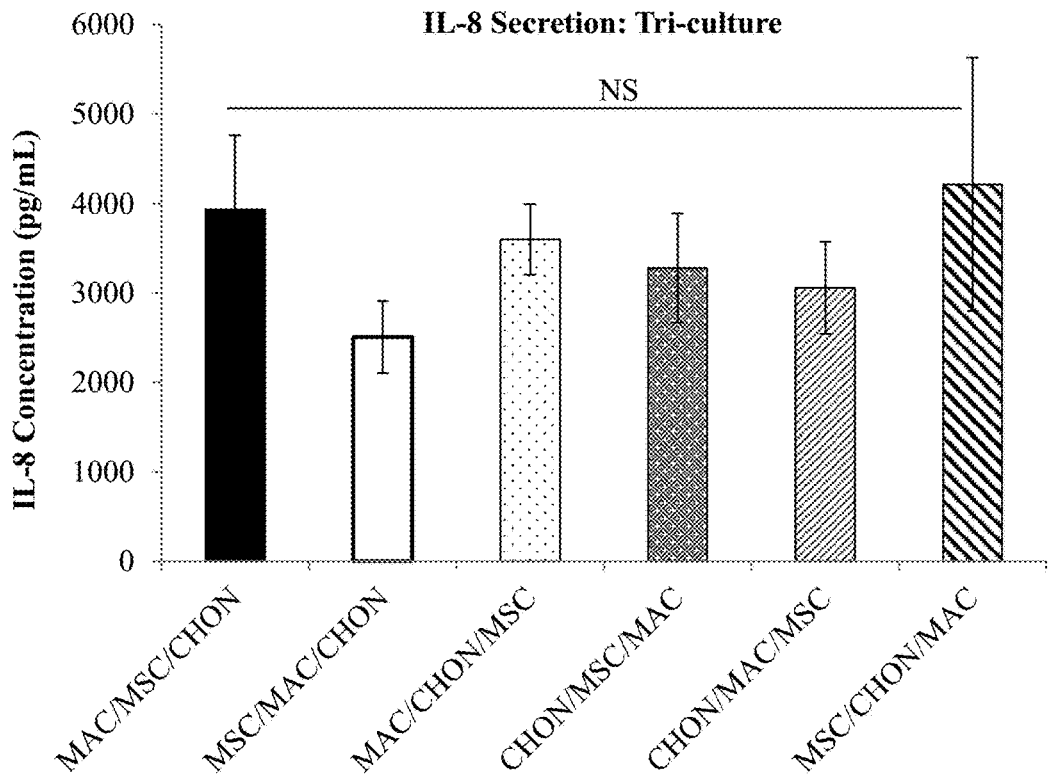
FIG. 19A) IL-8 and FIG. 19B) IL-6 were measured from the cell culture supernatants after 48 hours of culture. While IL-8 secretion levels in tri-culture were relatively similar to the addition of the individual cell type secretion, the IL-6 tri-culture secretion was in average 3 times higher than the combined individual cell secretions. X-axis indicates the configuration type and the location of the cells (Top/Middle/Bottom). CHO=chondrocytes, MAC=macrophages and MSC=mesenchymal stromal cells. Bar graphs represent the average total cell secretion±SEM (pg/mL) of n=6-11 samples from at least 3 independent experiments. NS=not significant.
Figure 19B:
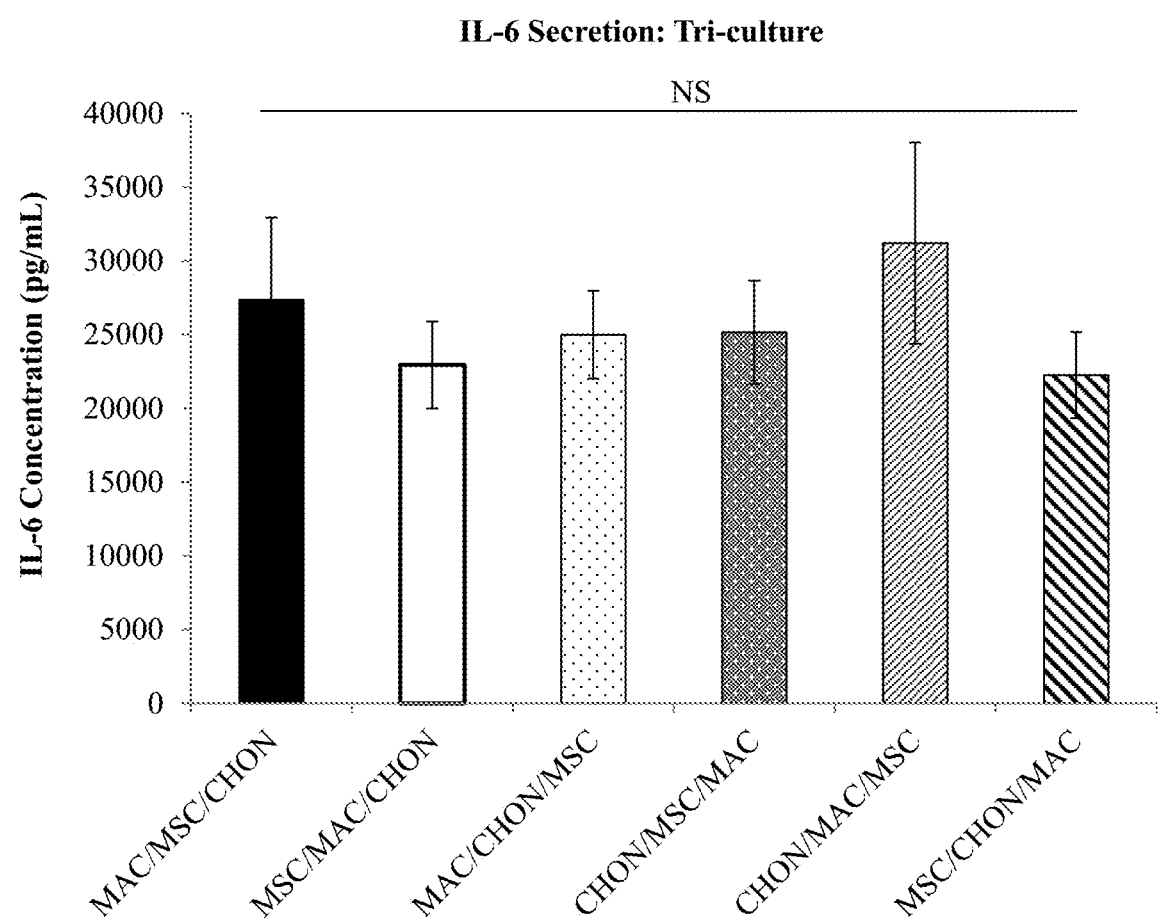
FIG. 19 shows total cell cytokine secretion in different tri-culture configurations.

Cell Functional Secretion. Similarly, we observed some variation (although not statistically significant) in total secretion levels of IL-8 (FIG. 19A) and IL-6 (FIG. 19B) for the tri-culture configurations when comparing the order of culture stacks. In addition, the average total IL-8 levels (3,431.64 pg/mL) produced by the tri-culture configurations was in the same order of magnitude when compared to the total IL-8 secretion levels (2,738 pg/mL) produced by chondrocytes, macrophages, and MSC cultured separately in individual stackable inserts. TNF-α was not detected in any of the configurations.

Remarkably, the average total IL-6 levels (25,653.52 pg/mL) produced by the tri-cultures were 3 times higher than the sum of total IL-6 secretion s (8,369.25 pg/mL) produced by individual cells cultured separately in the stackable inserts (Table 2). This demonstrates a dramatic synergistic and specific effect when 3 cell types are cultured together in a tri-culture configuration.

TABLE 2

In tri-culture configurations the IL-6 secretion levels are at least 3 times higher than the IL-6 sum of individual cell culture secretions (single chondrocytes, macrophages, and MSC) showing a synergistic effect. However, IL-8 secretion levels in tri-culture are similar to the IL-8 sum of individual cultures.

| Single Device Culture | IL-6 (pg/mL) | IL-8 (pg/mL) |
|---|---|---|
| Chondrocytes (CHON) | 592.49 | 955.16 |
| Macrophages (MAC) | 0 | 1,447.72 |
| Mesenchymal stromal cells (MSC) | 7,776.75 | 335.13 |
| Addition of cell secretion averages | 8,369.25 | 2,738.00 |

| Tri-culture Configurations | IL-6 (pg/mL) | IL-8 (pg/mL) |
|---|---|---|
| MAC/MSC/CHON | 27,365.57 | 3,934.75 |
| MSC/MAC/CHON | 22,948.77 | 2,505.54 |
| MAC/CHON/MSC | 24,993.99 | 3,598.81 |
| CHON/MSC/MAC | 25,155.43 | 3,280.13 |
| CHON/MAC/MSC | 31,202.14 | 3,057.31 |
| MSC/CHON/MAC | 22,255.24 | 4,213.28 |
| Average secretion | 25,653.52 | 3,431.64 |

What is claimed is:

1. A cell culture device comprising:
   a guide collar configured to fit inside a well of a tissue culture plate and having an inner wall defining an inner space having an axis that is parallel to the inner wall, the inner wall comprising a plurality of grooves;
   a plurality of membrane assemblies each comprising a planar microporous membrane on a membrane retainer, wherein each membrane retainer has a thickness between about 0.01 mm and about 1.55 mm and wherein each membrane assembly is dimensioned to fit within and translate through the inner space along the axis, and wherein the plurality of membrane assemblies includes:
   a first membrane assembly comprising a first planar microporous membrane and a first membrane retainer; and
   a second membrane assembly comprising a second planar microporous membrane and a second membrane retainer;
   wherein when the first and second membrane assemblies are positioned within the inner space and the first and second planar microporous membranes are orthogonal to the axis, the first and second planar microporous membranes are parallel to one another, and
   wherein the first membrane retainer, the second membrane retainer, or both the first membrane retainer and the second membrane retainer comprise a plurality of tabs, each positioned to engage a different one of the plurality of grooves.

2. The cell culture device of claim 1, wherein the plurality of membrane assemblies comprises at least three membrane assemblies.

3. The cell culture device of claim 1, wherein the first membrane retainer comprises a first tab and the inner wall of the guide collar includes one or more grooves, and wherein each of the one or more grooves is parallel to the axis and is configured to receive the first tab and direct the first membrane assembly as it translates through the inner space.

4. The cell culture device of claim 3, wherein when the first membrane assembly is positioned within the space and the first tab is engaged with a first groove of the one or more grooves, the first groove and the first tab inhibit rotation of the first membrane assembly about the axis.

5. The cell culture device of claim 1, wherein the second membrane retainer comprises a second tab, and wherein each of the one or more grooves is parallel to the axis and configured to receive the second tab and direct the second membrane assembly as it translates through the inner space.

6. The cell culture device of claim 1, wherein the first membrane retainer comprises a first notch and the inner wall of the guide collar includes a tab, wherein the tab is parallel to the axis and is configured to engage the first notch and direct the first membrane assembly as it translates through the inner space.

7. The cell culture device of claim 6, wherein when the first membrane assembly is positioned within the space and the tab is engaged with the first notch, the tab and the first notch inhibit rotation of the first membrane assembly about the axis.

8. The cell culture device of claim 6, wherein the second membrane retainer comprises a second notch, and wherein the tab is configured to engage the second notch and direct the second membrane assembly as it translates through the inner space.

9. The cell culture device of claim 6, wherein the inner wall of the guide collar includes a plurality of tabs, wherein the first membrane retainer comprises a plurality of first notches each positioned to engage a different one of the plurality of tabs, and wherein the second membrane retainer comprises a plurality of second notches each positioned to engage a different one of the one or more tabs.

10. The cell culture device of claim 1, wherein the microporous membrane comprises a polymeric material selected from a linear polycarbonate, a polyester of carbonic acid, a poly(vinylchloride), a polyamide, a polyethylene terephthalate, a styrene-acrylic acid copolymer, a polysulfone, a halogenated poly(vinylidene), a polychloroether, a poly(urethane) and a poly(imide).

11. The cell culture device of claim 10, wherein the pore size of the membrane is between about 0.2 μm and about 3.0 μm.

12. The cell culture device of claim 10, wherein the membrane retainer includes an aperture and the microporous membrane extends across the aperture.

13. The cell culture device of claim 1, wherein the microporous membrane is glass.

14. The cell culture device of claim 13, wherein the microporous membrane is between about 0.01 mm and about 0.025 mm thick.

15. The cell culture device of claim 13, wherein the microporous membrane comprises micropores between about 0.001 mm and about 0.003 mm in diameter.

16. The cell culture device of claim 13, wherein the membrane retainer comprises a biocompatible polymer adhered to the glass.

17. The cell culture device of claim 16, wherein the biocompatible polymer is SU8-2500.

18. The cell culture device of claim 10, wherein the membrane retainer is between about 0.02 mm and about 0.03 mm thick.

19. The cell culture device of claim 1, wherein the microporous membrane is coated with at least one biomaterial comprising a protein, a polypeptide, an amino acid, a polysaccharides, a monosaccharides or a combination thereof.

20. The cell culture device of claim 1, further comprising at least one spacer adapted to be positioned between the first membrane assembly and the second membrane assembly.

21. The cell culture device of claim 20, wherein the spacer has a shape and dimension corresponding to the inner wall of the guide collar such that the spacer translates through the inner space along and orthogonal to the axis.

22. The cell culture device of claim 20, wherein the spacer is comprised of glass.

23. The cell culture device of claim 20, wherein the spacer is between about 0.01 mm and about 1.55 mm thick.

24. A method for culturing cells in vitro comprising:
providing a cell culture device of claim 1;
inserting the guide collar into a well of a tissue culture plate;
placing cells on each of the microporous membranes;
inserting the first membrane assembly into the guide collar whereupon the first membrane assembly translates through the guide collar until the membrane retainer engages the bottom of the tissue culture plate and the microporous membrane is orthogonal to the axis;
inserting the second membrane assembly into the guide collar whereupon the second membrane assembly translates through the guide collar, the microporous membrane is orthogonal to the axis and the first and second planar microporous membranes are parallel to one another;
incubating the cells in a culture medium under conditions for cell growth.

25. The method of claim 24, wherein first membrane assembly engages with the second membrane assembly and wherein the distance between the first microporous membrane and the second microporous membrane is between about 0.01 mm and about 1.55 mm.

26. The method of claim 24, further comprising inserting a third membrane assembly into the guide collar whereupon the third membrane assembly translates through the guide collar and the microporous membrane is orthogonal to the axis and wherein the second membrane assembly engages with the third membrane assembly and the distance between the second microporous membrane and the third microporous membrane is between about 0.01 mm and about 1.55 mm.

27. The method of claim 26, further comprising selecting a plurality of spacers and positioning the plurality of spacers between the first membrane assembly and the second membrane assembly, the second membrane assembly and the third membrane assembly, or a combination thereof.

28. The method of claim 24, further comprising coating the microporous membrane with at least one biomaterial wherein the biomaterial comprises proteins, polypeptides, amino acids, polysaccharides, monosaccharides or a combination thereof.

29. The method of claim 24, further comprising incubating the membrane assemblies in a culture medium under conditions for cell growth separately prior to loading into the guide collar.

30. The method of claim 24, wherein the cells on each of the microporous membranes of the membrane assemblies are different types of cells.

31. The method of claim 24, wherein each of the membrane assemblies is loaded into the guide collar at approximately the same time.

32. A method for studying paracrine signaling in cells, the method comprising:
providing a cell culture device of claim 1;
placing cells on each of the microporous membranes;
inserting the guide collar into a well of a tissue culture plate;
inserting the first membrane assembly into the guide collar whereupon the first membrane assembly translates through the guide collar until the membrane retainer engages the bottom of the tissue culture plate and the microporous membrane is orthogonal to the axis;
inserting the second membrane assembly into the guide collar whereupon the second membrane assembly translates through the guide collar, the microporous membrane is orthogonal to the axis and the first and second planar microporous membranes are parallel to one another and wherein the first membrane assembly engages with the second membrane assembly and the distance between the first microporous membrane and the second microporous membrane is between about 0.01 mm and about 1.55 mm;
incubating the cells in a culture medium under conditions for growth;
monitoring changes in cell behavior, cellular structures, cell morphology, cellular biomarkers or a combination thereof.

33. The method of claim 32, further comprising inserting a third membrane assembly into the guide collar whereupon the third membrane assembly translates through the guide collar, the microporous membrane is orthogonal to the axis and the second and third planar microporous membranes are parallel to one another and wherein the second membrane assembly engages with the third membrane assembly and the distance between the second microporous membrane and the third microporous membrane is between about 0.01 mm and about 1.55 mm.

34. The method of claim 32, further comprising selecting the plurality of spacers and positioning the plurality of spacers between the first membrane assembly and the second membrane assembly, the second membrane assembly and the third membrane assembly, or a combination thereof.

35. The method of claim 32, further comprising coating the microporous membrane with at least one biomaterial wherein the biomaterial comprises proteins, polypeptides, amino acids, polysaccharides, monosaccharides or a combination thereof.

36. The method of claim 32, further comprising incubating the membrane assemblies in a culture medium under conditions for cell growth separately prior to loading into the guide collar.

37. The method of claim 32, wherein the cells on each of the microporous membranes of the membrane assemblies are different types of cells.

38. The method of claim 32, wherein each of the membrane assemblies is loaded into the guide collar at the same time.

* * * * *